(12) United States Patent
Koyama

(10) Patent No.: US 8,356,629 B2
(45) Date of Patent: Jan. 22, 2013

(54) MULTIWAY COCK AND LIQUID DISPENSING CIRCUIT

(75) Inventor: Shingo Koyama, Nakakoma-gun (JP)

(73) Assignee: Terumo Kabushiki Kaisha, Shibuya-ku, Tokyo (JP)

( * ) Notice: Subject to any disclaimer, the term of this patent is extended or adjusted under 35 U.S.C. 154(b) by 510 days.

(21) Appl. No.: 12/665,145

(22) PCT Filed: Mar. 26, 2008

(86) PCT No.: PCT/JP2008/055695
§ 371 (c)(1),
(2), (4) Date: Dec. 17, 2009

(87) PCT Pub. No.: WO2008/155938
PCT Pub. Date: Dec. 24, 2008

(65) Prior Publication Data
US 2010/0191106 A1    Jul. 29, 2010

(30) Foreign Application Priority Data
Jun. 20, 2007   (JP) ................................. 2007-163194

(51) Int. Cl.
*F16K 11/08* (2006.01)
*A61M 5/00* (2006.01)
(52) U.S. Cl. ............... 137/625.19; 137/625.47; 604/248
(58) Field of Classification Search ............. 137/625.19, 137/625.47; 604/32, 248
See application file for complete search history.

(56) References Cited

U.S. PATENT DOCUMENTS

| 246,538 | A | * | 8/1881 | Mullaney ....................... 137/595 |
| 627,019 | A | * | 6/1899 | Streubel ................... 137/625.16 |
| 988,658 | A | * | 4/1911 | Pfaff et al. ....................... 141/46 |
| 3,499,467 | A | * | 3/1970 | Lang, Jr. et al. ......... 137/625.19 |
| 4,776,730 | A | * | 10/1988 | Nearen et al. .................. 406/124 |
| 5,084,031 | A | * | 1/1992 | Todd et al. ..................... 604/248 |
| 5,097,840 | A | * | 3/1992 | Wallace et al. ................ 600/485 |

FOREIGN PATENT DOCUMENTS

| JP | 55-090767 A | 7/1980 |
| JP | 58-177631 C | 11/1983 |
| JP | 09-108360 A | 4/1997 |

OTHER PUBLICATIONS

International Search Report mailed on Jun. 17, 2008 by the Japanese Patent Office in its capacity as the International Searching Authority in International Application No. PCT/JP2008/055695.
Written Opinion mailed on Jun. 17, 2008 by the Japanese Patent Office in its capacity as the International Searching Authority in International Application No. PCT/JP2008/055695.

* cited by examiner

Primary Examiner — John Fox
(74) Attorney, Agent, or Firm — Buchanan Ingersoll & Rooney

(57) ABSTRACT

A multiway cock has a cock body, a cock member, and a cover. The cock body has a circular tube part that has a first portion and a second portion arranged parallel to each other along the axis of the circular tube part. A first port and a second port are formed in the outer periphery of the first portion, and a third port, a fourth port, a fifth port, and a sixth port are formed in the outer periphery of the second portion. The cock member has a barrel part in which a first flow passage and a second flow passage are formed, a lever installation part, and a lever. Opening or closing of the first to sixth ports formed in the first portion and the second portion can be selected by rotating the cock member.

13 Claims, 14 Drawing Sheets

(a)

(b)

MULTIWAY COCK AND LIQUID DISPENSING CIRCUIT

TECHNICAL FIELD

The present invention relates to a multiway cock and a liquid dispensing circuit.

BACKGROUND ART

As a method for treating coronary stenoses, a minimally invasive treatment using a catheter has become widespread. In performing this operation, infusion of a radiopaque material is carried out for checking the position of the catheter or the condition of the stenosed portion. In addition, flushing with physiological saline is appropriately conducted for securing an image contrast. Furthermore, while the circuit in the operation is constantly connected to a pressure monitor for measuring (detecting) and displaying the arterial blood pressure and the blood pressure is being checked, the connection to the pressure monitor is cut off at the time of introducing the radiopaque material or the physiological saline.

For performing each of these operations, the flow passage in the circuit has to be changed over. As means for changing over the flow passage, conventionally, a triplet of three-way cocks has been used.

In the case of the triplet of three-way cocks, however, there are three cocks and it is necessary to operate the three cocks. Therefore, the operation required is intricate, and thus it has been impossible to change over the flow passage swiftly.

In addition, for facilitating these operations, the device described in Patent Document 1, for example, has been known. In the device, however, changeover between a radiopaque material route (flow passage) and a pressure monitor route can only be performed, and changeover to a physiological saline route cannot be achieved. Further, an addition of a physiological saline route is difficult to realize, since such an addition leads to a complicated mechanism.

Patent Document 1:
Japanese Laid-Open Patent Publication No. 09-108360

DISCLOSURE OF INVENTION

An object of the present invention is to provide a multiway cock and a liquid dispensing circuit with which operations for changing over complicate flow passages can be carried out easily and speedily.

In order to achieve the above object, according to the present invention, there is provided a multiway cock including:

a cock body including a tubular part which has a first portion and a second portion juxtaposed to each other along an axis, at least two ports provided in the outer periphery of the first portion, and at least three ports provided in the outer periphery of the second portion; and a cock member having a barrel part rotatably inserted in the tubular part, the barrel part being formed with a first flow passage for opening in a predetermined combination the ports provided in the first portion, and a second flow passage for opening in a predetermined combination the ports provided in the second portion, wherein opening or closing of the ports provided in the first portion and the second portion is selected by rotating the cock member.

This ensures that operations for changing over complicate flow passages can be carried out easily and speedily.

In addition, since the first portion and the second portion are juxtaposed to each other along the axis of the tubular part, reduction in size can be contrived.

In the multiway cock according to the present invention, preferably, the first flow passage is so formed that predetermined two of the ports provided in the first portion can simultaneously be put into an open state or a closed state, and that a rotating angle range of the cock member where the predetermined two ports are in the open state is wider than a rotating angle range of the cock member where the predetermined two ports are in the closed state.

With this structure, operations for changing over complicate flow passages can be carried out easily and speedily.

In the multiway cock according to the present invention, preferably, the second flow passage is so formed that predetermined three of the ports provided in the second portion can simultaneously be put into an open state or a closed state, and that a rotating angle range of the cock member where the predetermined three ports are in the closed state is wider than a rotating angle range of the cock member where the predetermined three ports are in the open state.

With this structure, operations for changing over complicated flow passages can be carried out easily and speedily.

In the multiway cock according to the present invention, preferably, the first flow passage is so formed that predetermined two of the ports provided in the first portion can simultaneously be put into a closed state, the second flow passage is so formed that predetermined three of the ports provided in the second portion can simultaneously be put into an open state, and the predetermined two ports in the first portion are in the closed state when the predetermined three ports in the second portion are in the open state.

With this structure, operations for changing over complicate flow passage can be carried out easily and speedily.

In the multiway cock according to the present invention, preferably, the first flow passage is so formed that predetermined two of the ports provided in the first portion can simultaneously be put into an open state or a closed state, the second flow passage is so formed that predetermined three of the ports provided in the second portion can simultaneously be put into an open state or a closed state, and in the operation of rotating the cock member, the timing of transition of the predetermined two ports in the first portion from the closed state to the open state and the timing of transition of the predetermined three ports in the second portion from the open state to the closed state are the same.

In this way, when transition of the predetermined two ports in the first portion from the closed state to the open state and transition of the predetermined three ports in the second portion from the open state to the closed state are effected by rotating the cock member, it is possible to avoid a condition where both of the predetermined two ports and the predetermined three ports are in the open state. In addition, it is possible to shorten the period in which both of the predetermined two ports and the predetermined three ports are in the closed state.

In the multiway cock according to the present invention, preferably, the first flow passage is so formed that predetermined two of the ports provided in the first portion can simultaneously be put into an open state or a closed state, the second flow passage is so formed that predetermined three of the ports provided in the second portion can simultaneously be put into an open state or a closed state, and in the operation of rotating the cock member, the timing of transition of the predetermined two ports in the first portion from the closed state to the open state is close to the timing of transition of the predetermined three ports in the second portion from the open state to the closed state, and the predetermined two ports in the first portion transit from the closed state to the open state after the predetermined three ports in the second portion transit from the open state to the closed state.

In this manner, when transition of the predetermined two ports in the first portion from the closed state to the open state and transition of the predetermined three ports in the second portion from the open state to the closed state are effected by rotating the cock member, it is possible to avoid a condition where both of the predetermined two ports and the predetermined three ports are in the open state. In addition, it is possible to shorten the period in which both of the predetermined two ports and the predetermined three ports are in the closed state.

In the multiway cock according to the present invention, preferably, the first flow passage has a first part provided in an outer peripheral surface of the barrel part and extended in the circumferential direction of the barrel part, a second part located on the opposite side of a center axis of the barrel part from the first part and extended in the circumferential direction of the barrel part, and a third part which penetrates the barrel part and connects the first part to the second part.

With this structure, it is possible to make the first flow passage such that predetermined two of the ports provided in the first portion can simultaneously be put into the open state or the closed state, and that the rotating angle range of the cock member where the predetermined two ports are in the open state is wider than the rotating angle range of the cock member where the predetermined two ports are in the closed state.

In the multiway cock according to the present invention, preferably, the cock body has, in the outer periphery of the first portion, the first port and the second port arranged side by side along the circumferential direction thereof, and has, in the outer periphery of the second portion, the third port, the fourth port, the fifth port and the sixth port arranged sequentially side by side along the circumferential direction thereof, the first port, the second port and the third port are each in a closed state whereas the fourth port, the fifth port and the sixth port are each in an open state when the cock member is positioned in a first position, and the first port, the second port and the fifth port are each in the closed state whereas the third port, the fourth port and the sixth port are each in the open state when the cock body is positioned in the second position.

With this structure, operations for changing over complicate flow passages can be carried out easily and speedily.

In the multiway cock according to the present invention, preferably, the first port and the second port are in the open state, and the third port, the fourth port and the fifth port are in the open state and the sixth port is in the closed state when the cock member is positioned in a third position provided in the course of movement of the cock member from the first position to the second position.

With this structure, operations for changing over complicate flow passages can be carried out easily and speedily.

In the multiway cock according to the present invention, preferably, the first port and the second port are in the open state whereas the third port, the fourth port, the fifth port and the sixth port are in the closed state when the cock member is positioned in a fourth position provided in the course of movement of the cock member from the first position to the third position and when the cock member is positioned in a fifth position provided in the course of movement of the cock member from the third position to the second position.

With this structure, operations for changing over complicate flow passages can be carried out easily and speedily.

In the multiway cock according to the present invention, preferably, the first port and the third port are projected in the same direction, and the second port and the fifth port are projected in the same direction.

This enables the cock member to be rotated with the first port and the third port as a mark and with the second port and the fifth port as another mark.

In the multiway cock according to the present invention, preferably, the first port is connected to a flow passage leading to a blood vessel of a patient, the second port is connected to a flow passage leading to pressure detecting means, the third port is connected to a flow passage leading to a vessel in which a radiopaque material is contained, the fourth port is connected to a flow passage leading to the blood vessel of the patient, the fifth port is connected to a flow passage leading to a vessel in which physiological saline is contained, and the sixth port is connected to liquid feeding means directly or through a tube.

This ensures that, after the cock member is positioned into the first position, infusion of the physiological saline into the patient's blood vessel can be performed by only operating the liquid feeding means, without rotating the cock member.

In addition, after the cock member is positioned into the second position, infusion of the radiopaque material into the patient's blood vessel can be performed by only operating the liquid feeding means, without rotating the cock member.

In the multiway cock according to the present invention, preferably, the first flow passage and the second flow passage are not communicating with each other.

With this structure, it is not necessary to provide means for disconnecting the first flow passage and the second flow passage or for releasing the disconnection, whereby the configuration can be simplified.

In the multiway cock according to the present invention, preferably, the cock member has an operating part for rotating the cock member.

With this structure, it is possible to rotate the cock member can easily.

Further, in order to attain the above object, according to the present invention, there is provided a liquid dispensing circuit including the multiway cock according to the invention.

This ensures that, at the time of dispensing a liquid, changeover of complicated flow passages can be performed easily and speedily.

BEST MODE FOR CARRYING OUT THE INVENTION

The multiway cock and the liquid dispensing circuit according to the present invention will be described in detail below, based on a preferred embodiment shown in the attached drawings.

Figure 1:
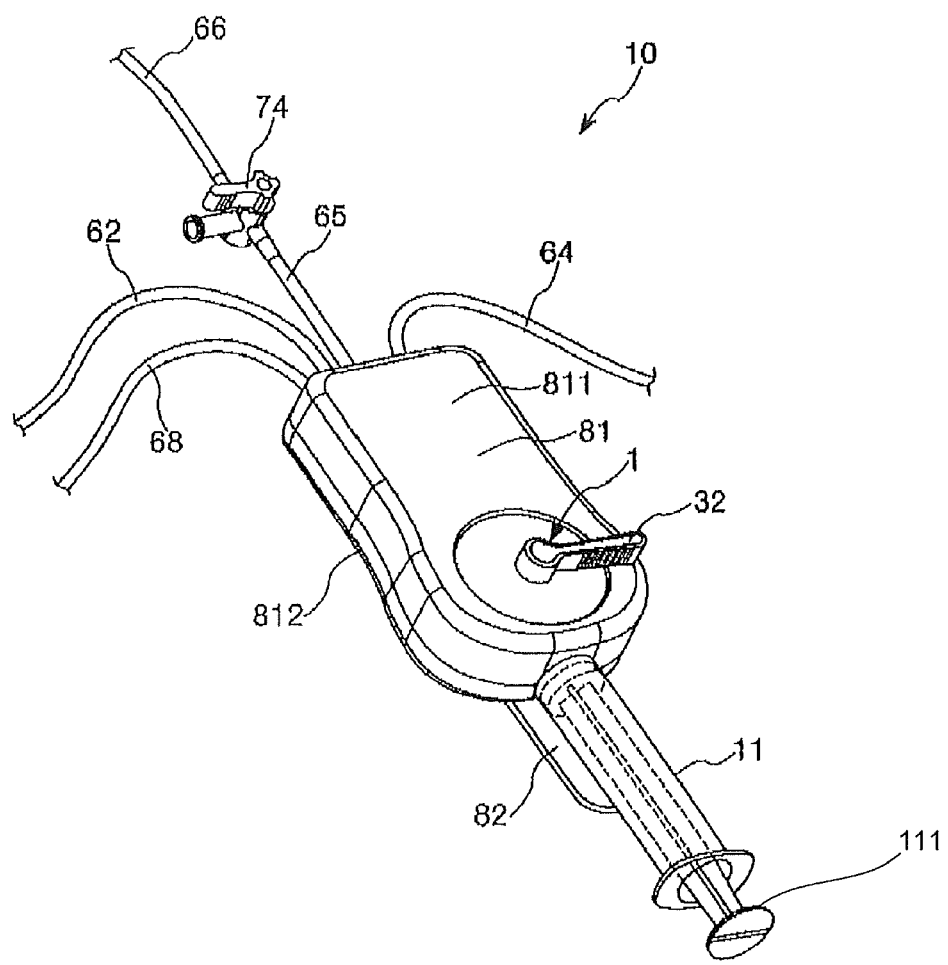
FIG. 1 is a perspective view of an embodiment of the liquid dispensing circuit according to the present invention.
Figure 2:
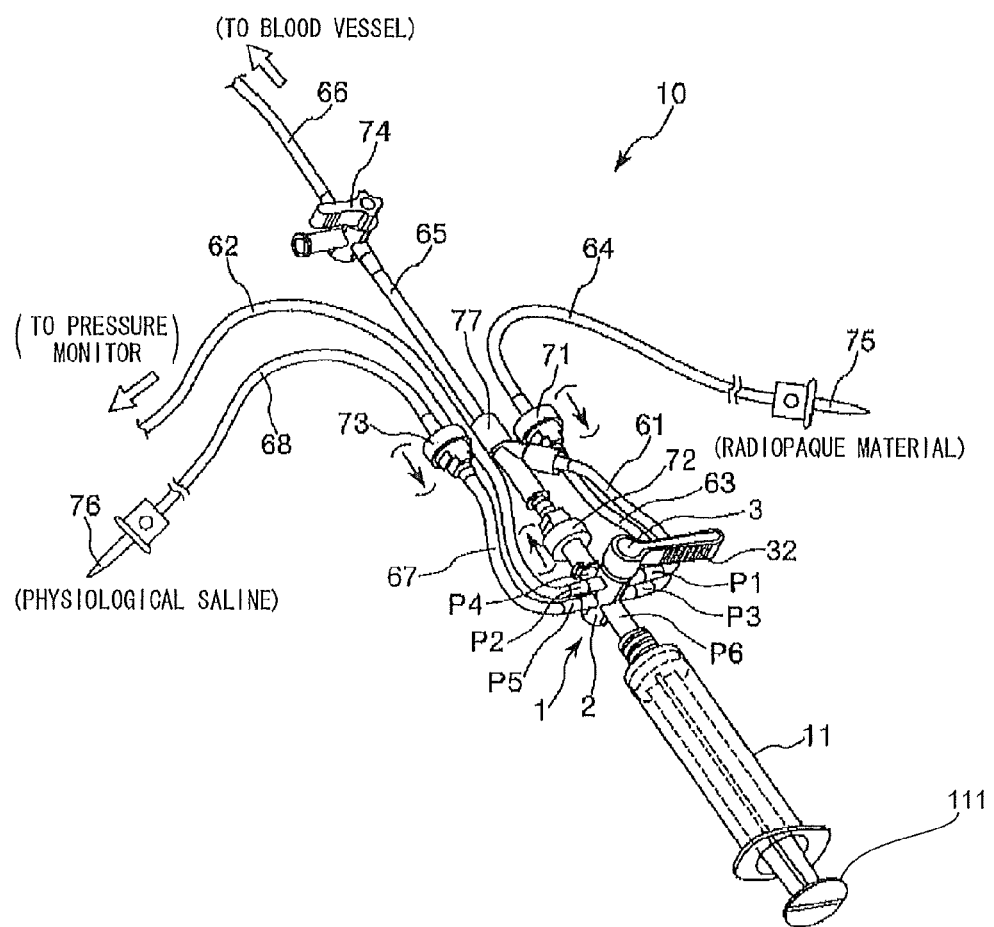
FIG. 2 is a perspective view of the liquid dispensing circuit shown in FIG. 1, in the condition where a casing has been removed.
Figure 3:
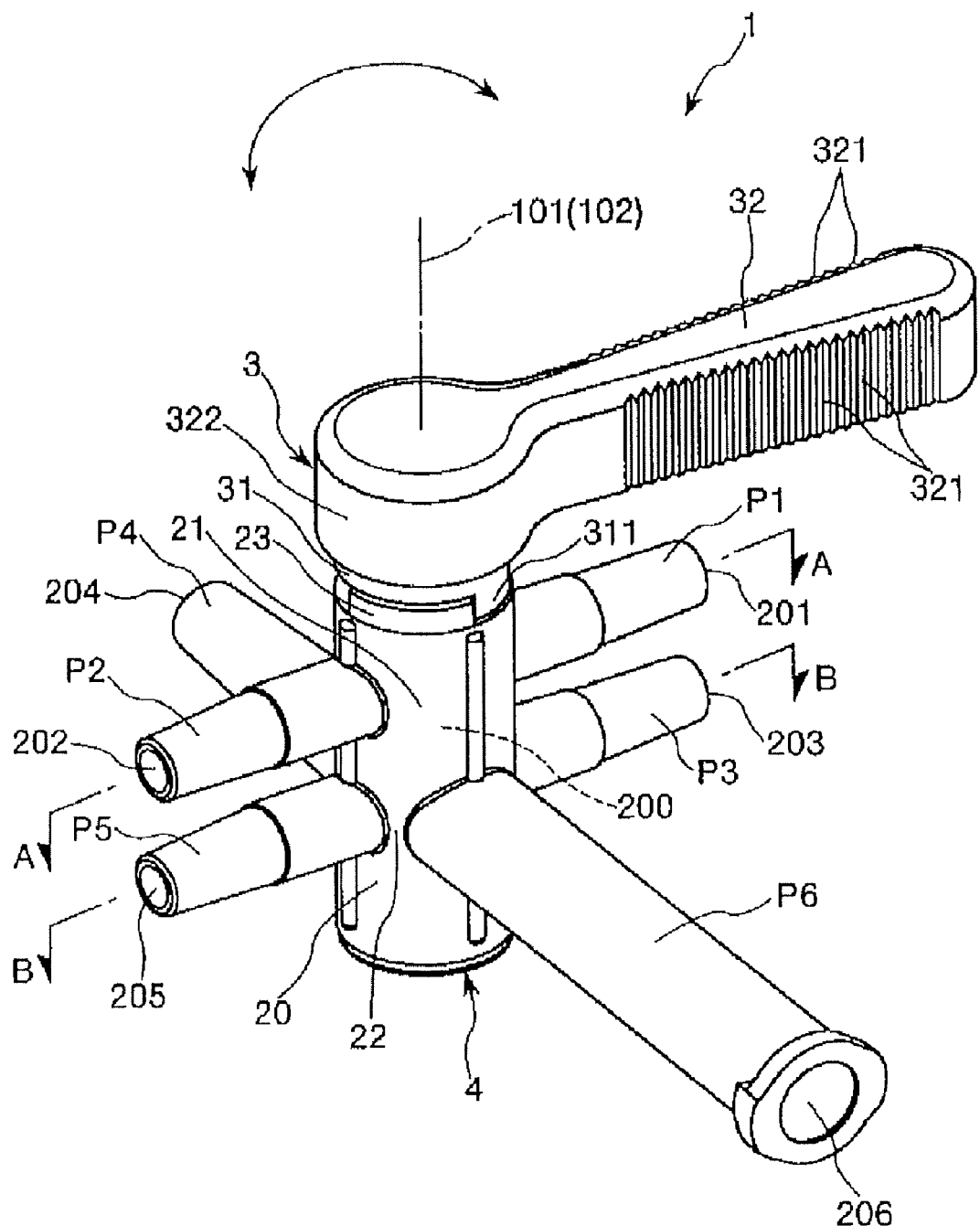
FIG. 3 is a perspective view of a multiway cock (an embodiment of the multiway cock according to the present invention) in the liquid dispensing circuit shown in FIG. 1.
Figure 4:
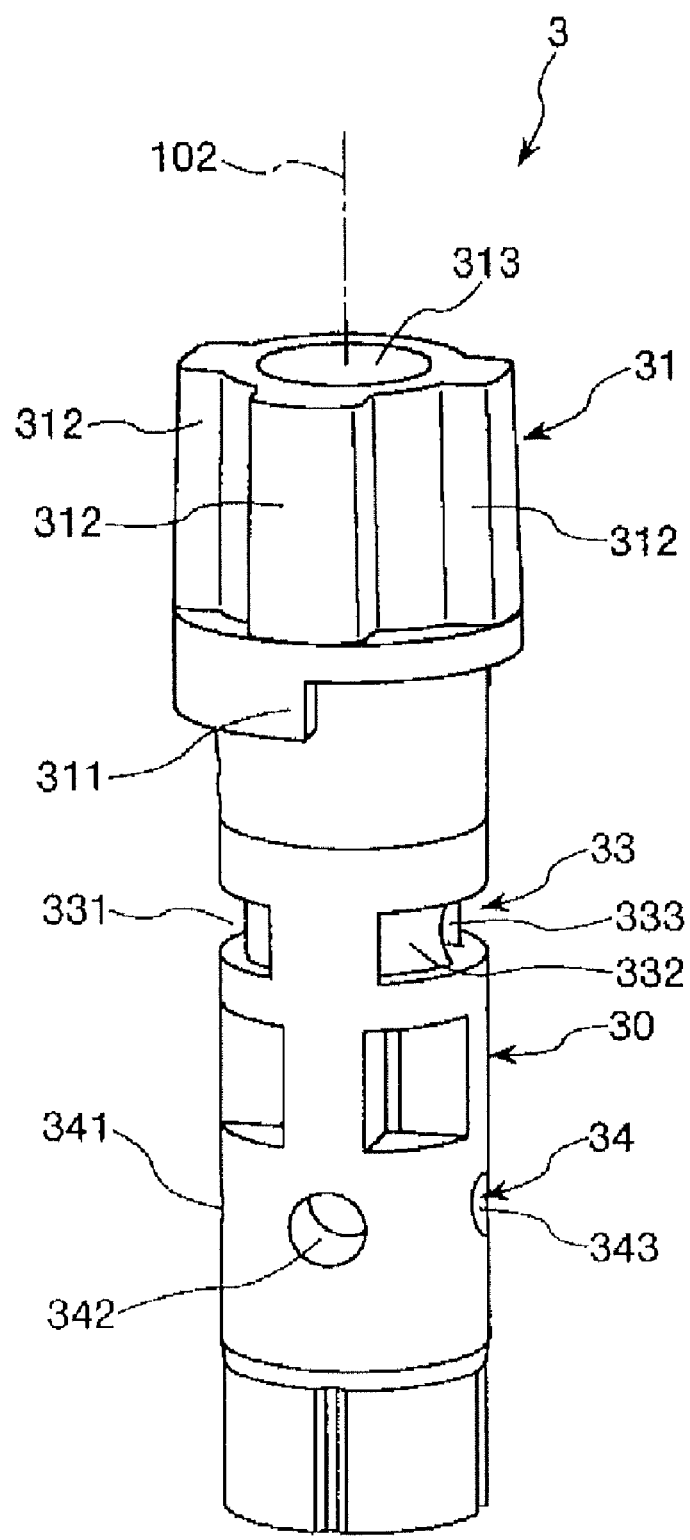
FIG. 4 is a perspective view of a cock member in the multiway cock shown in FIG. 3.
Figure 5:
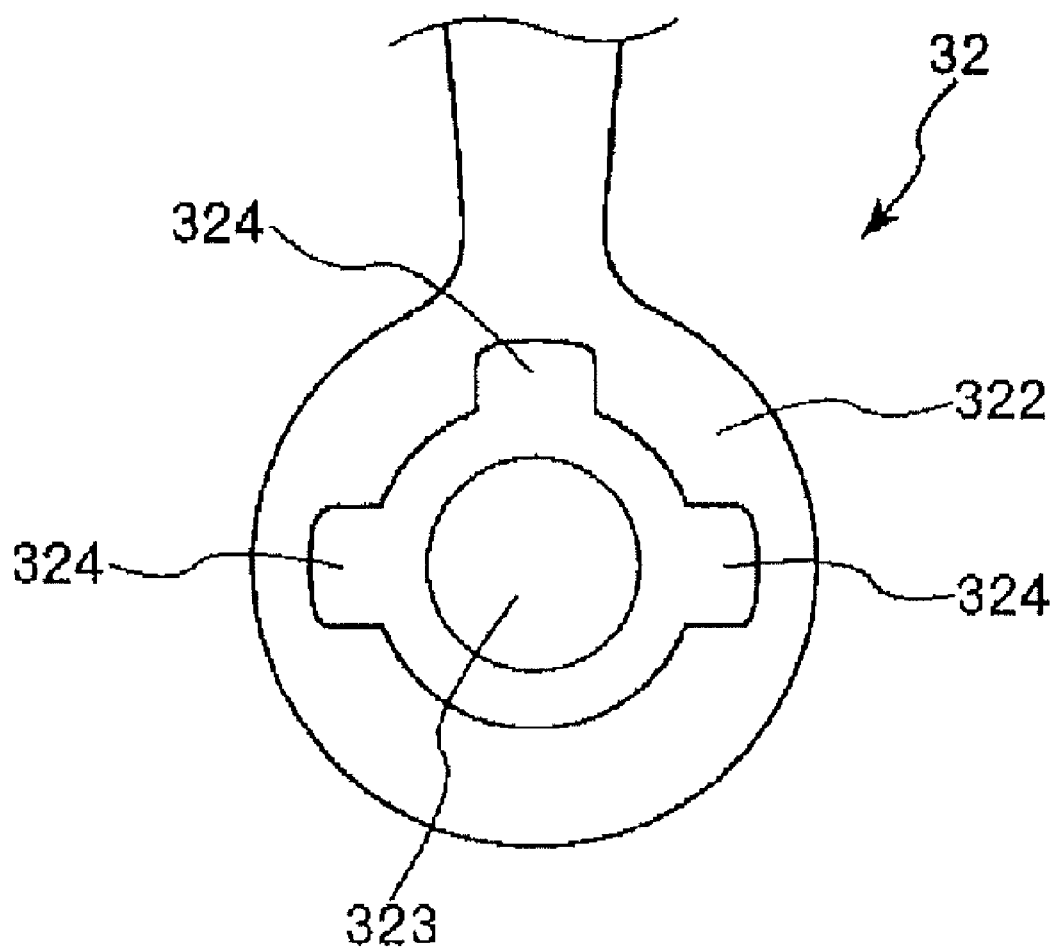
FIG. 5 is a back view of a rotational central part of a lever of the multiway cock shown in FIG. 3.
Figure 13:
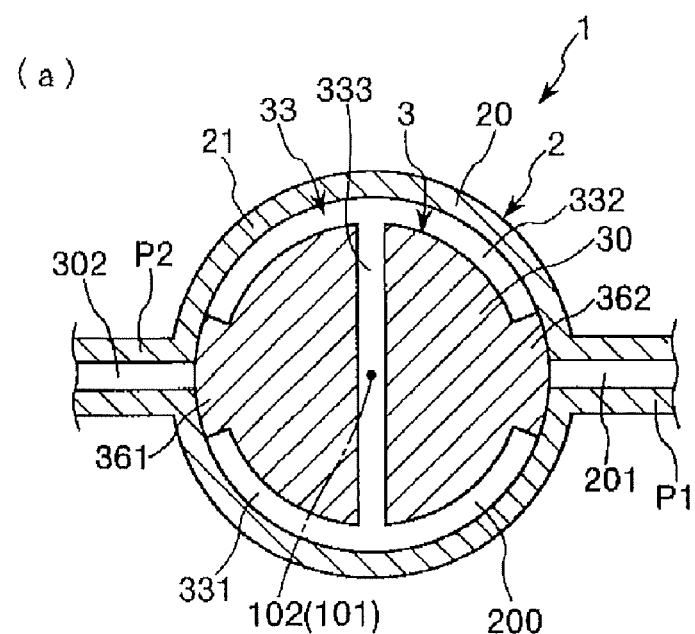
FIG. 13 illustrates cross-sectional views for schematically illustrating a flow passage changeover pattern in the multiway cock shown in FIG. 3.
Figure 13:
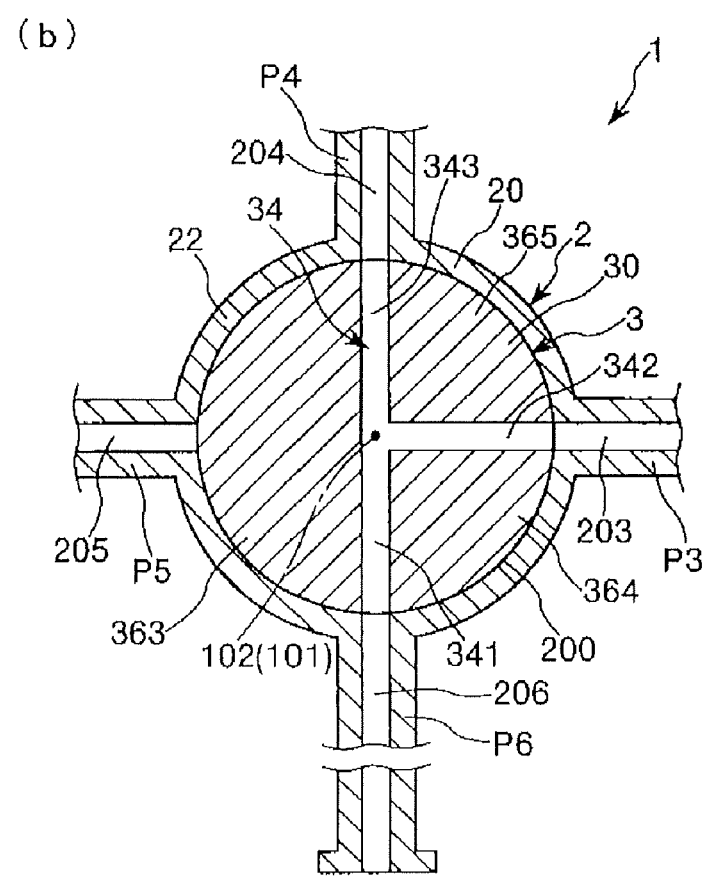
Figure 14:
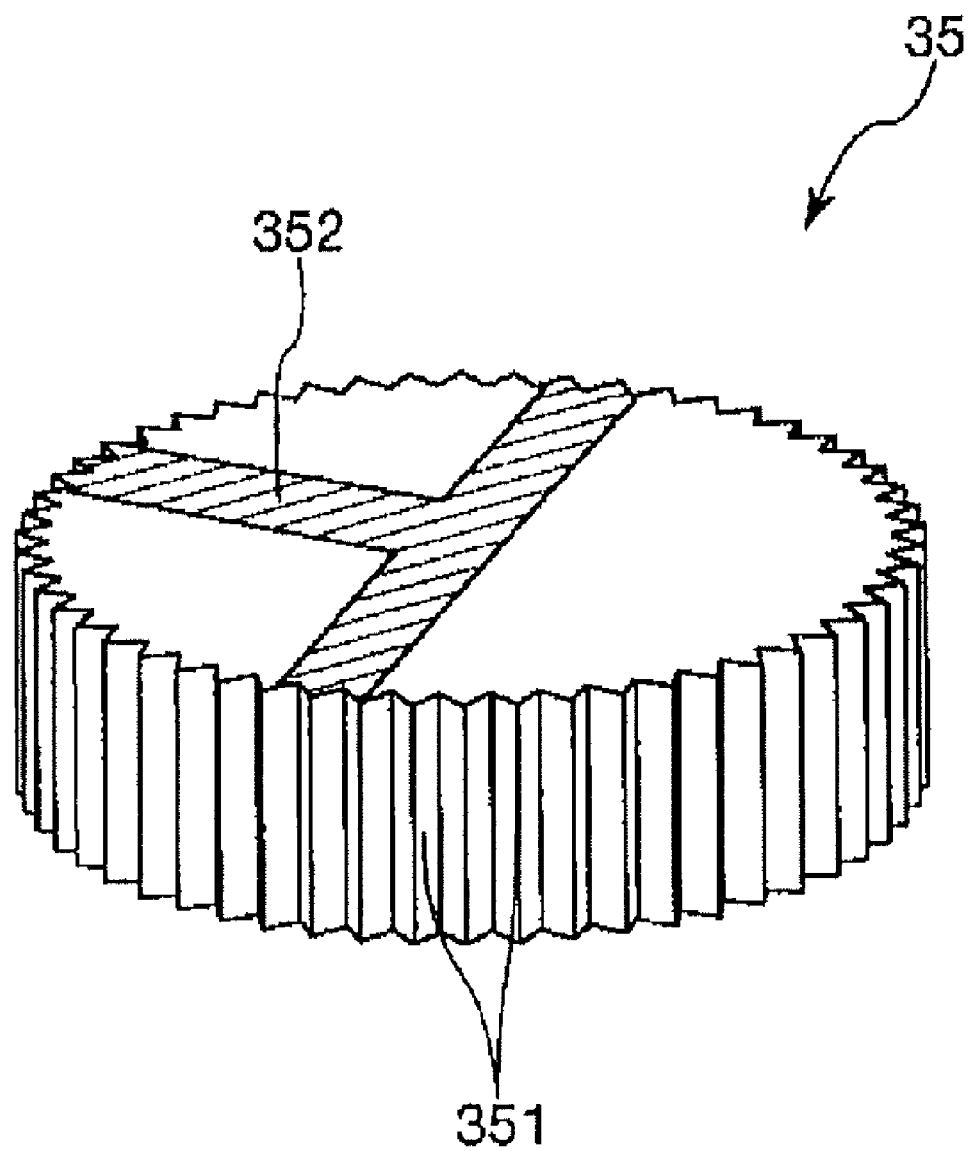
FIG. 14 is a perspective view of another configuration example of an operating part of the cock member.

FIG. 1 is a perspective view of an embodiment of the liquid dispensing circuit according to the present invention; FIG. 2 is a perspective view of the liquid dispensing circuit shown in FIG. 1, in the condition where a casing has been removed; FIG. 3 is a perspective view of a multiway cock (an embodiment of the multiway cock according to the present invention) in the liquid dispensing circuit shown in FIG. 1; FIG. 4 is a perspective view of a cock member in the multiway cock shown in FIG. 3; and FIG. 5 is a back view of a rotational central part of a lever of the multiway cock shown in FIG. 3. In addition, FIGS. 6 to 13 show cross-sectional views for schematically illustrating flow passage changeover patterns in the multiway cock shown in FIG. 3, wherein FIGS. 6(*a*) to 13(*a*) show sectional views taken along line A-A of FIG. 3, and FIGS. 6(*b*) to 13(*b*) show sectional views taken along line B-B of FIG. 3. Further, FIG. 14 is a perspective view of another configuration example of an operating part of a cock member.

For convenience of explanation, the upper side in FIGS. 3 and 4 will be referred to as "upper" or "upper end," and the lower side in the figures will be referred to as "lower" or "lower end."

The liquid dispensing circuit 10 shown in these figures is, for example, a circuit (device) to be used in a treatment of coronary stenosis for dispensing (infusion) each of physiological saline and a radiopaque material into a patient (a person for whom the circuit is used).

As shown in FIGS. 1 and 2, the liquid dispensing circuit 10 includes a multiway cock (flow passage changeover means) 1, tubes 61 to 68, check valves 71 to 73, a three-way cock (medicine dispensing cock) 74, air vent integrated type bottle needles 75, 76, and a branch connector 77 composed of a three-way branch pipe (T-pipe, Y-pipe, non-right angled T-pipe, or the like), and a casing 81 for accommodating a part (most part) of these components.

First, the multiway cock 1 will be described.

As shown in FIGS. 3 to 6, the multiway cock (flow passage changeover means) 1 is a two-stage multiway cock, which includes a cock body 2, a cock member 3, and a cover 4.

The cock body 2 has a thick-walled hollow cylindrical part (tubular part) 20, and the hollow cylindrical part 20 has a first portion 21 and a second portion 22 juxtaposed to each other along the axis (center axis) 101 thereof. In the configuration shown in the figures, the first portion 21 is disposed on the upper side (at an upper stage), and the second portion 22 is disposed on the lower side (at a lower stage). The first portion 21 may be disposed on the lower side and the second portion 22 may be disposed on the upper side, contrary to the above-mentioned layout.

In the outer periphery of the first portion 21, a first port P1 and a second port P2 composed of pipes (branch pipes) projecting outwards in radial directions (directions perpendicular to the axis 101) at an angular interval of 180° are provided (formed) side by side along the circumferential direction. In addition, flow passages 201 and 202 formed inside the first port P1 and the second port P2 communicate with an inner cavity 200 of the hollow cylindrical part 20 at the same height.

Further, a third port P3, a fourth port P4, a fifth port P5 and a sixth port P6 composed of pipes (branch pipes) projecting outwards in radial directions (directions perpendicular to the axis 101) at an angular interval of 90° are provided (formed) sequentially side by side along the circumferential direction. Specifically, the third port P3, the fourth port P4, the fifth port P5 and the sixth port P6 are arranged in this order such that the third port P3 and the first port P1 project in the same direction and the fifth port P5 and the second port P2 project in the same direction. Incidentally, in plan view (as viewed from the upper side in FIG. 3), the third port P3 and the first port P1 coincide (overlap) with each other, and the fifth port P5 and the second port P2 coincide with each other. Further, flow passages 203, 204, 205 and 206 formed inside the third to sixth ports P3 to P6 communicate with the inner cavity 200 of the hollow cylindrical part 20 at the same height.

In addition, tip portions of the first to third ports P1 to P3 and the fifth port P5 are gradually decreased in outside diameter toward the tip end. In other words, the tip portions are gradually decreasing outside diameter portions (in a tapered shape). This ensures that tubes or the like can be easily connected (linked) to the tip portions of the first to third ports P1 to P3 and the fifth port P5.

Further, a tip portion of the fourth port P4 is formed with a male luer taper. This enables a female luer taper or the like to be easily connected to the tip portion of the fourth port P4.

In addition, a tip portion of the sixth port P6 is formed with a female luer taper. This enables a syringe or the like to be easily connected to the tip portion of the sixth port P6.

The cock member 3 has a barrel part (insertion part) 30, a lever installation part 31, and a lever (operating part) 32. Opening or closing of the first to sixth ports P1 to P6 provided in the first portion 21 and the second portion 22 is selected by rotating the cock member 3, namely, rotating the cock member 3 (in a normal direction or a reverse direction) relative to the cock body 2.

The barrel part 30 is cylindrical in shape, and is rotatably inserted (fitted) in the inner cavity 200 of the hollow cylindrical part 20 in a gas-tight or liquid-tight fashion. Therefore, it is preferable that the outside diameter of the barrel part 30 in the condition where the cock member 3 has been pulled out of the hollow cylindrical part 20 is slightly larger than the inside diameter of the hollow cylindrical part 20, by about 1% to 6%, for example.

The barrel part 30 is provided, in its portion corresponding to the first portion 21, with a first flow passage 33 for opening the first port P1 and the second port P2 formed in the first portion 21 (for opening the ports in a predetermined combination, in the case where the number of the ports is three or more).

The first flow passage 33 is so formed that the first port P1 and the second port P2 can simultaneously be put into an open state or a closed state (predetermined two of the ports can simultaneously be put into an open state or a closed state, in the case where the number of the ports is three or more) and that the rotational angle range of the cock member 3 where the first port P1 and the second port P2 are in the open state is wider than the rotational angle range of the cock member 3 where the first port P1 and the second port P2 are in the closed state.

Specifically, the first flow passage 33 is composed of a first part 331 formed in the outer peripheral surface of the barrel part 30 and extended in the circumferential direction of the barrel part 30, a second part 332 located on the opposite side of the center axis 102 of the barrel part 30 from the first part 331 and extended in the circumferential direction of the barrel part 30, and a third part 333 which penetrates the barrel part 30 and through which the first part 331 and the second part 332 communicate with each other. More specifically, the first part 331 and the second part 332 are arcuate in shape and are provided in symmetry about the center axis 102. In addition, the third part 333 is rectilinear (bar-like) in shape, passes through the center axis 102, and makes a central portion of the first part 331 and a central portion of the second part 332 communicate with each other therethrough.

The first to third parts 331 to 333 are formed at such a height as to coincide with the flow passages 201 and 202 inside the ports P1 and P2 in the condition where the cock member 3 is fitted in the cock body 2 (this condition will be referred to simply as "cock member fitted condition").

Figure 6:
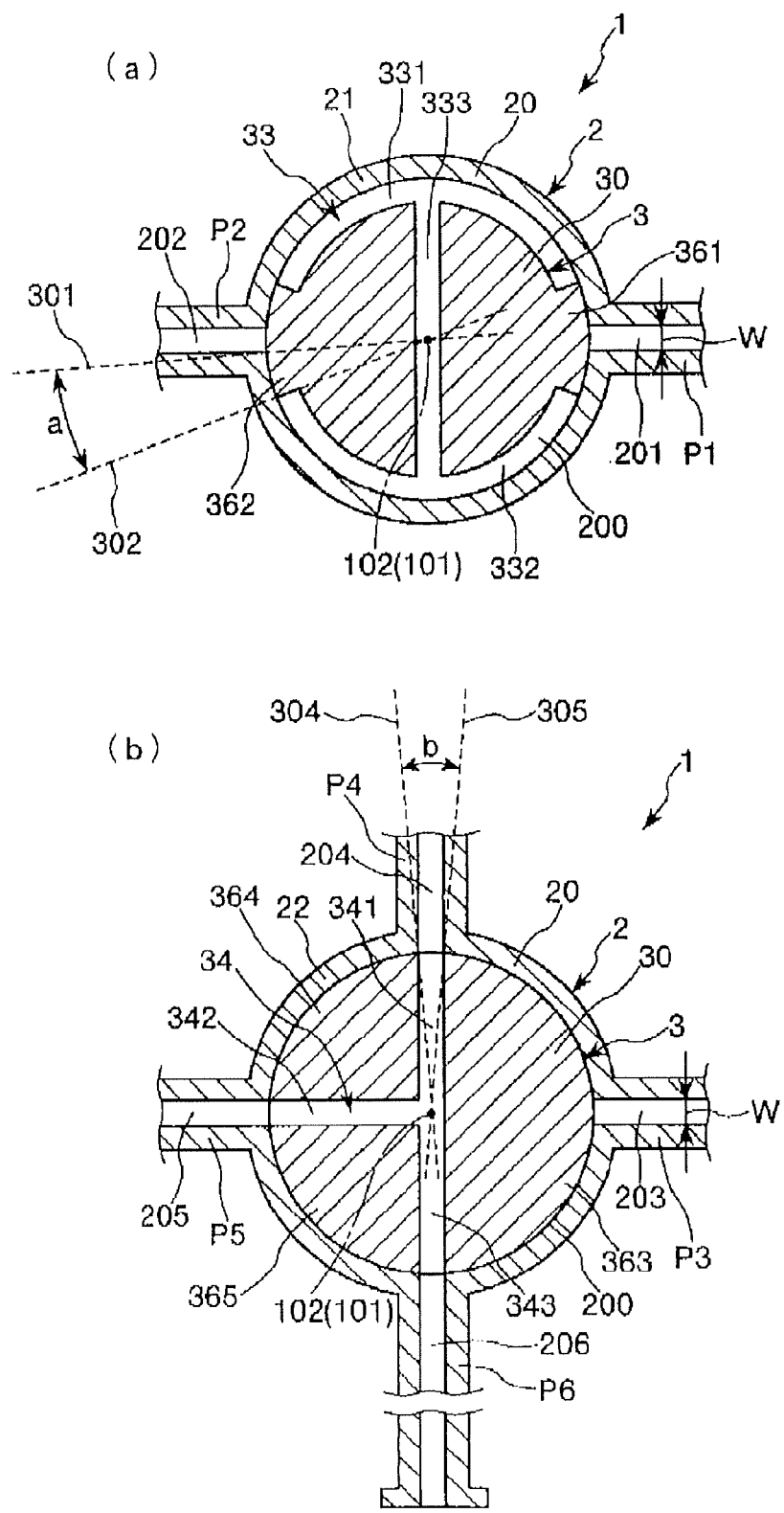
FIG. 6 illustrates cross-sectional views for schematically illustrating a flow passage changeover pattern in the multiway cock shown in FIG. 3.

Of the outer peripheral portion (outer peripheral surface) of the barrel part 30, the part between an end portion on the right side in FIG. 6 of the first part 331 and an end portion on the right side in FIG. 6 of the second part 332 constitutes a sealing part 361 for sealing (closing) the first port P1 and the second port P2 individually, and the part between an end portion on the left side in FIG. 6 of the first part 331 and an end portion on the left side in FIG. 6 of the second part 332 constitutes a sealing part 362 for sealing (closing) the first port P1 and the second port P2 individually.

In addition, the barrel part 30 is provided, in its portion corresponding to the second portion 22, with a second flow passage 34 for opening in a predetermined combination the third to sixth ports P3 to P6 formed in the second portion 22.

The second flow passage 34 is so formed that predetermined three of the third to sixth ports P3 to P6 can simultaneously be put into an open state or a closed state and that the rotational angle range of the cock member 3 where the predetermined three ports are in the closed state is wider than the rotational angle range of the cock member 3 where the predetermined three ports are in the open state.

Specifically, the second flow passage 34 is formed in T-shape. More specifically, the second flow passage 34 is composed of a first part 341, a second part 342 and a third part 343 which are extended in radial directions of the barrel part 30 at an angular interval of 90° and which communicate with one another near a central portion of the barrel part 30. In this case, the first part 341, the second part 342 and the third part 343 are arranged in this order and in such a manner that, in plan view, the first part 341 and the third part 343 coincide with the third part 333 of the first flow passage 33. In addition, the first to third parts 341 to 343 are opened in the outer peripheral surface of the barrel part 30, forming circular openings (tip openings).

The first to third parts 341 to 343 are formed at such a height as to coincide with the flow passages 203 to 206 in the ports P3 to P6 in the cock member fitted condition.

Further, the second flow passage 34 and the first flow passage 33 do not communicate with each other. This ensures that opening/closing of the first port P1 and the second port P2 formed in the first portion 21 and opening/closing of the third to sixth ports P3 to P6 formed in the second portion 22 can be controlled independently.

Of the outer peripheral portion (outer peripheral surface) of the barrel part 30, the part on the right side in FIG. 6 relative to the first part 341 and the third part 343 constitutes a sealing part 363 for sealing (closing) the third port P3, the fifth port P5 and the sixth port P6 individually; the part between an end portion on the upper side in FIG. 6 of the first part 341 and an end portion on the left side in FIG. 6 of the second part 342 constitutes a sealing part 364 for sealing (closing) the third port P3 and the fourth port P4 individually; and the part between an end portion on the left side in FIG. 6 of the second part 342 and an end portion on the lower side in FIG. 6 of the third part 343 constitutes a sealing part 365 for sealing (closing) the fourth port P4 and the fifth port P5 individually.

Incidentally, while the widths w (inside diameters) of the flow passages 201 to 206, the first to third parts 331 to 333 of the first flow passage 33 and the first to third parts 341 to 343 of the second flow passage 34 are all set to be equal in the configuration shown in the figure, widths w may naturally be different.

As shown in FIG. 4, a lever installation part (operating part installation part) 31 which is larger than the outside diameter of the barrel part 30 and to which a lever 32 is mounted (fitted) is provided at an upper portion of the barrel part 30. Preferably, the barrel part 30 and the lever installation part 31 are formed integrally. In the cock member fitted condition, the lever installation part 31 is exposed on the upper side of the hollow cylindrical part 20.

As shown in FIG. 3, a bar-like lever 32 extending (projecting) in one direction is mounted on the lever installation part 31 so as to protrude outwards in a radial direction. In the condition where the lever 32 is mounted on the lever installation part 31, a rotational central part 322 of the lever 32 is fitted over the lever installation part 31. As will be described later, the lever 32 is prevented from rotating relative to the lever installation part 31, and the cock member 3 is rotated by gripping the lever 32 with fingers of a hand and applying a torque. For this purpose, the lever 32 is provided in both its side surfaces with projection-and-recess patterns 321 as anti-slipping means.

As shown in FIG. 4, the lever installation part 31 is cylindrical in shape, and is provided in its outer periphery with three ribs 312 extended along the direction of the center axis 102 at an angular interval of 90°.

On the other hand, as shown in FIGS. 3 and 5, the rotational central part 322 of the lever 32 has a bottomed hollow cylindrical shape, and is formed at its central portion with a cylindrical projecting portion 323 to be inserted (fitted) into an inner cavity 313 of the lever installation part 31. In addition, the rotational central part 322 is provided in its inner periphery with three grooves 324 which are extended along the direction of the center axis 102 at an angular interval of 90° and in which the three ribs 312 of the lever installation part 31 are to be inserted.

The ribs 312 and the grooves 324 are arranged in such a manner that, in the condition where the lever 32 is mounted on the lever installation part 31, the extending direction of the lever 32 coincides with the projecting direction of the second part 342 of the second flow passage 34 from the center axis 102.

The ribs 312 and the grooves 324 ensure that, when the lever 32 is mounted on the lever installation part 31, the positional relationship of the lever 32 (the projecting direction of the lever 32) with the lever installation part 31 and the barrel part 30 is restricted to the above-mentioned one.

Further, when the lever 32 is rotated (subjected to a rotating operation) relative to the cock body 2, the ribs 312 and inside surfaces (side surfaces) of the grooves 324 are put into contact (engagement) with each other, whereby rotation of the lever 32 relative to the lever installation part 31 and the barrel part 30 is prevented from occurring. Consequently, the cock member 3 as a whole is rotated as one body relative to the cock body 2.

As shown in FIG. 3, at the outer periphery of an upper portion of the hollow cylindrical part 20, a belt-like projection 23 is formed to project upwards. The projection 23 is formed over a center angle range of 90°.

On the other hand, as shown in FIG. 4, at the outer periphery of a lower portion of the lever installation part 31, a belt-like projection 311 capable of coming into contact (engagement) with the projection 23 in the cock member fitted condition is formed to project downwards. The projection 311 is formed over a center angle range of 90°.

As shown in FIG. 3, when the cock member 3 is rotated clockwise in FIG. 3 relative to the cock body 2, the projection 311 comes into abutment on (engagement with) an end portion on the right side in FIG. 3 of the projection 23, resulting in that the cock member 3 cannot be rotated any more clockwise in FIG. 3. The position of the cock member 3 in this instance is a second position, where the positional relationships between the first to sixth ports P1 to P6 of the cock body 2 and the barrel part 30 (the first flow passage 33 and the second flow passage 34) of the cock member 3 are as shown in FIG. 13.

In addition, when the cock member 3 is rotated by 180° counterclockwise in FIG. 3 from the second position relative to the cock body 2, the projection 311 comes into contact with an end portion on the left side in FIG. 3 of the projection 23, resulting in that the cock member 3 cannot be rotated any more counterclockwise in FIG. 3. The position of the cock member 3 in this instance is a first position, where the positional relationships between the first to sixth ports P1 to P6 of the cock body 2 and the barrel part 30 (the first flow passage 33 and the second flow passage 34) of the cock member 3 are as shown in FIG. 6.

Thus, by the projections 23 and 311, the cock member 3 is positioned individually into the first position and the second position and the rotational angle range of the cock member 3 relative to the cock body 2 is restricted to 180°, whereby it is possible to avoid a condition where the third port P3, the fifth port P5 and the sixth port P6 are in the open state. Accordingly, the projections 23 and 311 constitute rotational angle restricting means and positioning means.

In addition, the lever 32 functions also as an indicator for indicating the positional relationships between the first to sixth ports P1 to P6 of the cock body 2 and the barrel part 30 of the cock member 3 (the first flow passage 33 and the second flow passage 34), particularly, for indicating those ones of the third to sixth ports P3 to P6 which are in the open state. For instance, as will be described later, of the third to sixth ports P3 to P6, the one projecting in the same direction as the projecting direction of the lever 32 and two ports on both sides of the one port are in the open state. Therefore, the condition can be grasped by checking the position (projecting direction) of the lever 32.

Incidentally, the operating part for rotating the cock member 3 is not limited to the lever 32 shown in the drawings. For example, the operating part may be a part extended in two or more directions, a handle, a dial or the like.

As shown in FIG. 14, in the case where a circular disc-shaped dial 35 is used as the operating part, the dial 35 is provided in its outer peripheral surface (side surface) with a projection-and-recess pattern 351 as anti-slipping means.

In addition, the dial 35 is provided on its upper surface (the surface on the upper side in FIG. 14) with an indicator 352 for indicating the positional relationships of the first to sixth ports P1 to P6 of the cock body 2 and the barrel part 30 of the cock member 3 (the first flow passage 33 and the second flow passage 34), particularly, for indicating those ones of the third to sixth ports P3 to P6 which are in the open state. In the configuration shown in the figure, the shape of the indicator 352 is the same as the shape of the second flow passage 34 in plan view, namely, T-shape. In this case, the dial 35 is so mounted that the T-shape of the second flow passage 34 and the T-shape of the indicator 352 coincide (overlap) with each other in plan view. This ensures that, of the third to sixth ports P3 to P6, the three ports projecting in the same directions as the three projecting directions of the indicator 352 are in the open state, and this condition can be grasped by checking the indicator 352.

As shown in FIG. 3, a cover (sealing member) 4 is a member having a projected portion (not shown) at its central portion, and is mounted to the lower end of the hollow cylindrical part 20 of the cock body 2 so as to seal the lower end of the inner cavity 200.

In this case, the projecting portion of the cover 4 is fitted (secured) in a hole (not shown) formed in a lower end portion of the barrel part 30. This ensures that the barrel part 30 of the cock member 3 is prevented from slipping in the direction of the axis 101 relative to the hollow cylindrical part 20 of the cock body 2 or falling off.

Incidentally, the cover 4 may be secured to the hollow cylindrical part 20, instead of being secured to the barrel part 30.

Materials for constituting the cock body 2, the cock member 3 and the cover 4 are not particularly limited. Examples of the materials which can be used include various resins, for example, polyolefins such as polyethylene, polypropylene, polybutadiene, polyurethane, polystyrene, acrylic resins such as polymethyl methacrylate, polycarbonate, polyamides, polyesters such as polyethylene terephthalate, polyacetal, ABS resins, AS resins, fluororesins such as ionomer; various thermoplastic elastomers based on polyurethane, polyester, polyamide, olefin, styrene or the like; various metallic materials such as stainless steel, aluminum, titanium; and various glass materials, which may be used either singly or in an arbitrary combination (e.g., as a composite material).

Incidentally, in order to secure visibility of the inside of the multiway cock 1, for example, the cock body 2 may be formed by use of a light-transmitting material (transparent or translucent material).

Here, as shown in FIG. 6, in the condition where the cock member 3 is positioned in the first position, the angle between a straight line 301 passing through the center axis (center) 102 of the barrel part 30 and through the lower end in FIG. 6 of the base end of the flow passage 202 of the second port P2 and a straight line 302 passing through the center axis 102 and through the left end in FIG. 6 of the second part 332 of the first flow passage 33, in plan view (as viewed from the upper side in FIG. 3), is referred to as "a", and the angle between a straight line 304 passing through the center axis 102 and through the left end in FIG. 6 of the tip opening of the first part 341 of the second flow passage 34 and a straight line 305 passing through the center axis 102 and through the right end in FIG. 6 of the tip opening of the first part 341 of the second flow passage 34 is referred to as "b" (the same is also applied to other corresponding parts), then the first flow passage 33 and the second flow passage 34 are configured (set) so as to satisfy the condition of a≧b (a>b or a=b). In the case where a>b, it is preferable that "a" is slightly (a little) greater than "b".

In the configuration shown in the figure, "a" is slightly (a little) greater than "b". With this structure, as will be described later, when the cock member 3 is rotated (subjected to a rotating operation) clockwise in FIG. 3, the timing of transition of the first port P1 and the second port P2 from the closed state to the open state is close to the timing of transition of the fourth port P4, the fifth port P5 and the sixth port P6 from the open state to the closed state, and the first port P1 and the second port P2 transit from the closed state to the open state after the fourth port P4, the fifth port P5 and the sixth port P6 transit from the open state to the closed state.

In addition, where a=b unlike in the configuration shown in the figure, when the cock member 3 is rotated (subjected to a rotating operation) clockwise in FIG. 3, the timing of transition of the first port P1 and the second port P2 from the closed state to the open state and the timing of transition of the fourth port P4, the fifth port P5 and the sixth port P6 from the open state to the closed state are the same.

Now, operations of the multiway cock 1 will be described below.

[1] When the position of the lever 32 of the cock member 3 is in the same direction as the second port P2 and the fifth port P5, as shown in FIG. 6, the cock member 3 is positioned in the first position, the flow passage 201 of the first port P1, the flow passage 202 of the second port P2 and the flow passage 203 of the third port P3 are each sealed by the outer peripheral surface of the barrel part 30, and the flow passage 204 of the fourth port P4, the flow passage 205 of the fifth port P5 and the flow passage 206 of the sixth port P6 communicate with one another through the second flow passage 34 formed in the barrel part 30 of the cock member 3. This results in that the first port P1, the second port P2 and the third port P3 are each in the closed state, whereas the fourth port P4, the fifth port P5 and the sixth port P6 are each in the open state. Further, in this instance, the projection 311 of the cock member 3 is in abutment on the end portion on the left side in FIG. 3 of the projection 23 of the cock body 2, so that the cock member 3 cannot be rotated any more counterclockwise in FIG. 3.

Figure 7:
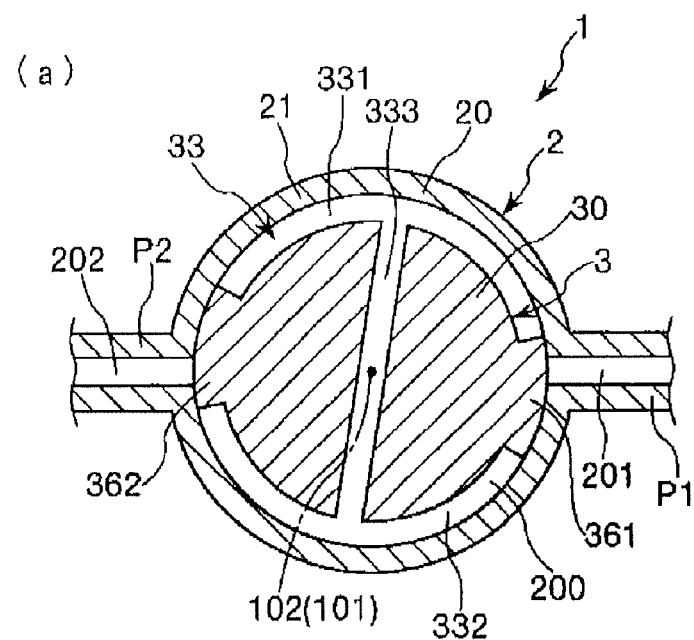
FIG. 7 illustrates cross-sectional views for schematically illustrating a flow passage changeover pattern in the multiway cock shown in FIG. 3.
Figure 7:
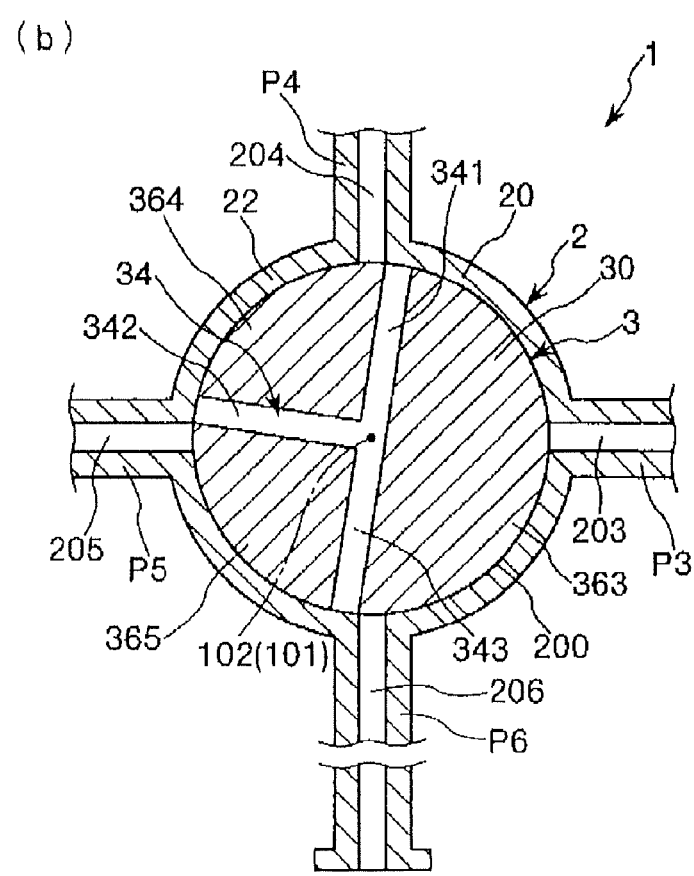

[2] When the cock member 3 is rotated (subjected to a rotating operation) clockwise in FIG. 3 by gripping the lever 32 by fingers of a hand and applying a torque with the result that the cock member 3 is positioned in the position shown in FIG. 7, the flow passage 201 of the first port P1, the flow passage 202 of the second port P2 and the flow passage 203 of the third port P3 are each maintained in the state of being sealed with the outer peripheral surface of the barrel part 30, whereas the flow passage 204 of the fourth port P4, the flow passage 205 of the fifth port P5 and the flow passage 206 of the sixth port P6 are each changed over to the state of being sealed with the outer peripheral surface of the barrel part 30. As a result, the first port P1, the second port P2 and the third port P3 are each maintained in the closed state, whereas the fourth port P4, the fifth port P5 and the sixth port P6 are each changed over from the open state to the closed state.

Thus, in this configuration, when the fourth port P4, the fifth port P5 and the sixth port P6 are in the open state, the first port P1 and the second port P2 are in the closed state.

Figure 8:
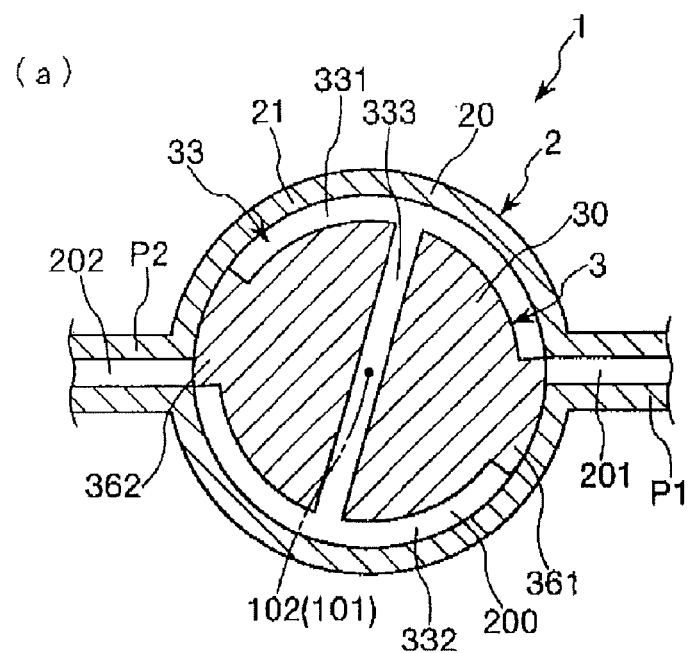
FIG. 8 illustrates cross-sectional views for schematically illustrating a flow passage changeover pattern in the multiway cock shown in FIG. 3.
Figure 8:
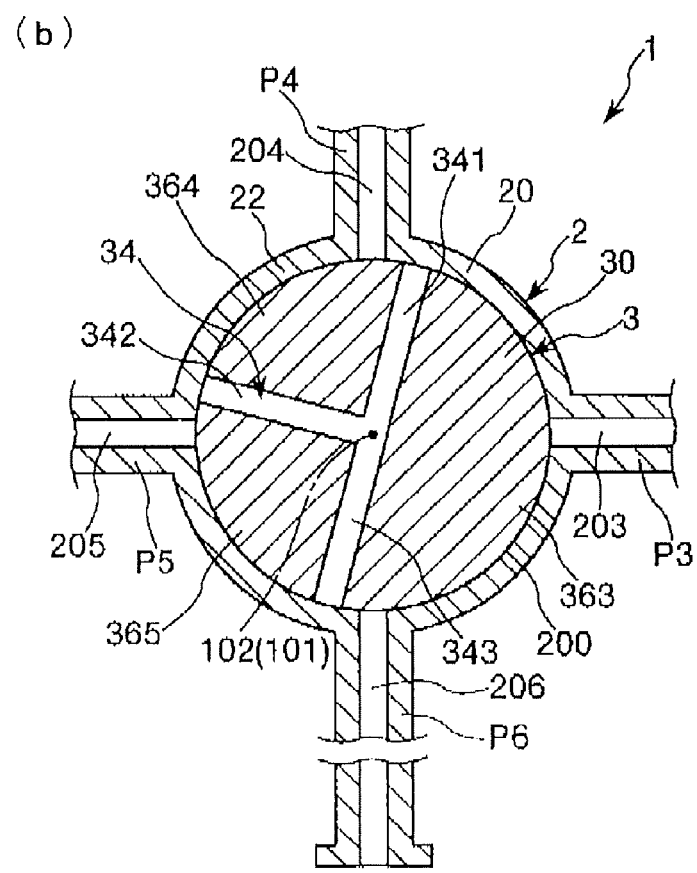

[3] When the cock member 3 is further rotated slightly clockwise in FIG. 3 and the cock member 3 is positioned into the position shown in FIG. 8 is a condition immediately before the flow passage 201 of the first port P1 and the flow passage 202 of the second port P2 come to communicate with each other through the first flow passage 33 formed in the barrel part 30 of the cock member 3. Immediately after this condition, the system is changed over to a condition where the flow passage 201 of the first port P1 and the flow passage 202 of the second port P2 communicate with each other through the first flow passage 33, whereby the first port P1 and the second port P2 are each changed over from the closed state to the open state.

When the cock member 3 is thus rotated (subjected to a rotating operation) clockwise in FIG. 3, the timing of transition of the first port P1 and the second port P2 from the closed state to the open state is close to the timing of transition of the fourth port P4, the fifth port P5 and the sixth port P6 from the open state to the closed state, and the first port P1 and the second port P2 transit from the closed state to the open state after the fourth port P4, the fifth port P5 and the sixth port P6 transit from the open state to the closed state.

Figure 9:
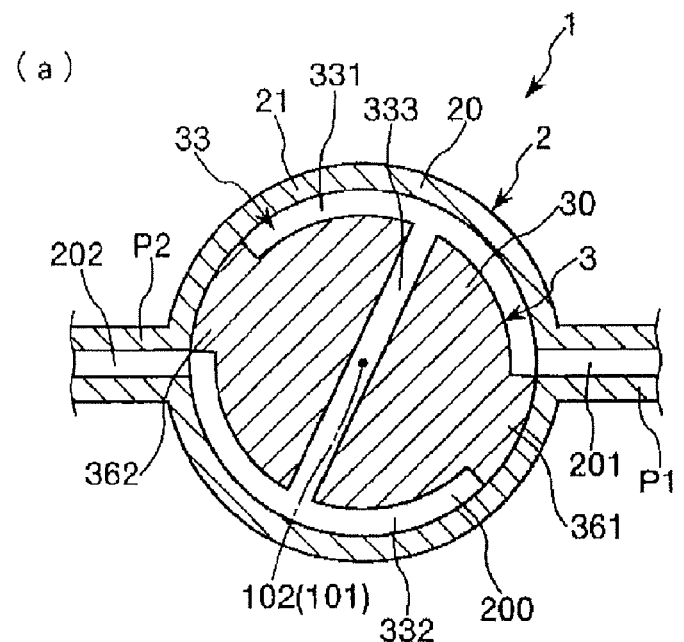
FIG. 9 illustrates cross-sectional views for schematically illustrating a flow passage changeover pattern in the multiway cock shown in FIG. 3.
Figure 9:
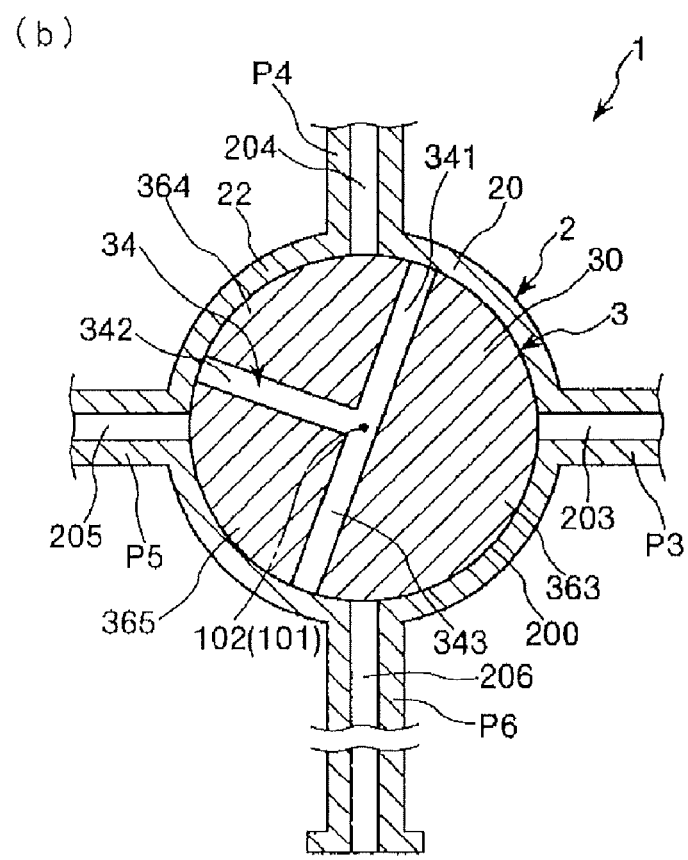

When the cock member 3 is positioned in the position shown in FIG. 9, the flow passage 201 of the first port P1 and the flow passage 202 of the second port P2 are communicating with each other through the first flow passage 33, whereas the flow passage 203 of the third port P3, the flow passage 204 of the fourth port P4, the flow passage 205 of the fifth port P5 and the flow passage 206 of the sixth port P6 are each being sealed with the outer peripheral surface of the barrel part 30. At this position, the first port P1 and the second port P2 are in the open state, whereas the third port P3, the fourth port P4, the fifth port P5 and the sixth port P6 are each in the closed state.

Figure 10:
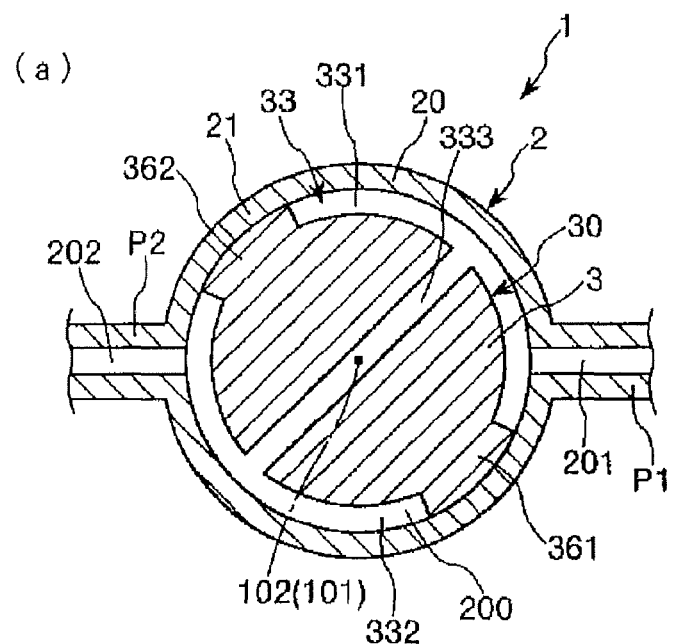
FIG. 10 illustrates cross-sectional views for schematically illustrating a flow passage changeover pattern in the multiway cock shown in FIG. 3.
Figure 10:
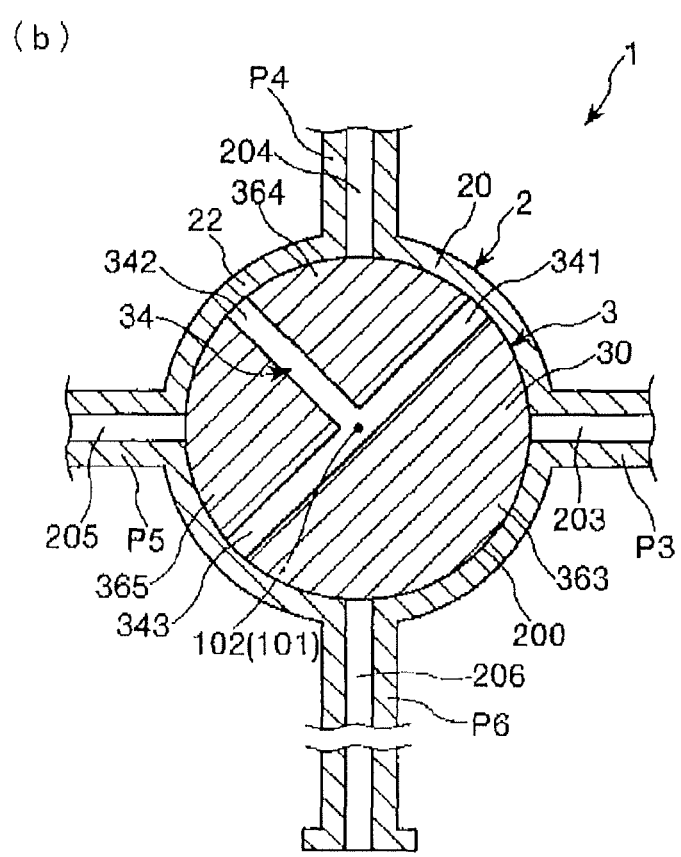

[4] When the cock member 3 is further rotated clockwise in FIG. 3 with the result that the cock member 3 is positioned in the fourth position shown in FIG. 10, the flow passage 201 of the first port P1 and the flow passage 202 of the second port P2 communicate with each other through the first flow passage 33, whereas the flow passage 203 of the third port P3, the flow passage 204 of the fourth port P4, the flow passage 205 of the fifth port P5 and the flow passage 206 of the sixth port P6 are each being sealed with the outer peripheral surface of the barrel part 30. That is, the first port P1 and the second port P2 are in the open state, whereas the third port P3, the fourth port P4, the fifth port P5 and the sixth port P6 are each in the closed state.

Figure 11:
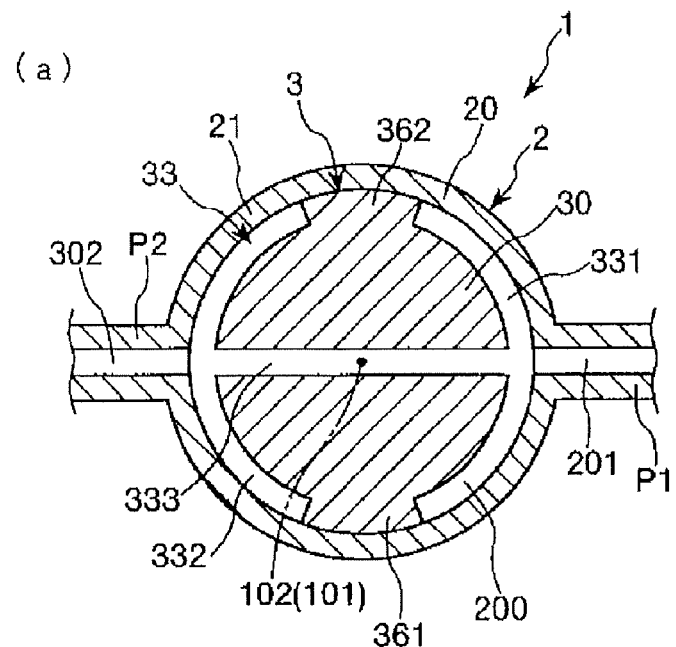
FIG. 11 illustrates cross-sectional views for schematically illustrating a flow passage changeover pattern in the multiway cock shown in FIG. 3.
Figure 11:
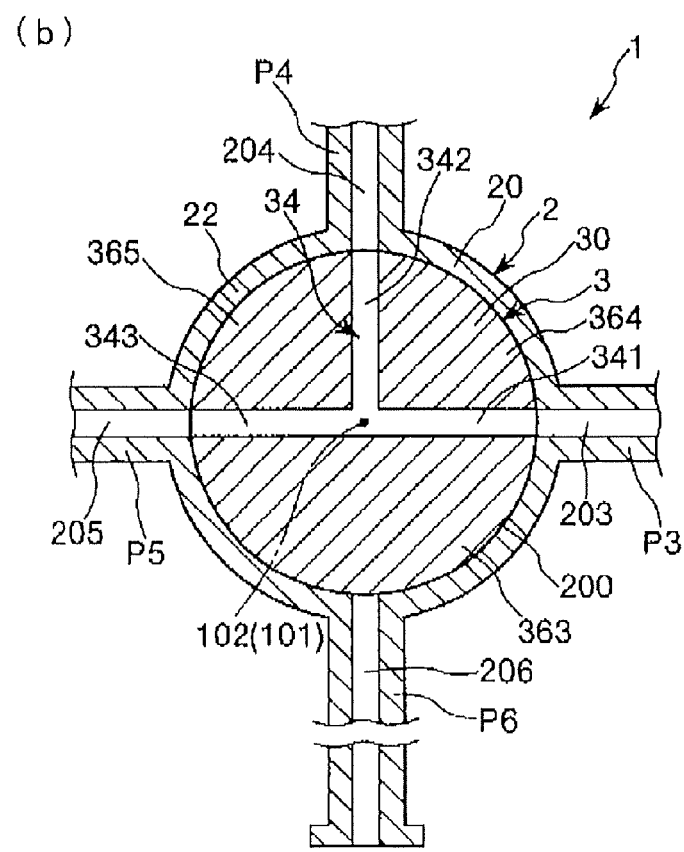

The fourth position is located in the course of the movement of the cock member 3 from the first position shown in FIG. 6 to a third position shown in FIG. 11 (in the example shown in the figures, the fourth position is located in the middle of the movement from the first position to the third position).

[5] When the cock member 3 is further rotated clockwise in FIG. 3 and positioned in the third position shown in FIG. 11, the flow passage 201 of the first port P1 and the flow passage 202 of the second port P2 communicate with each other through the first flow passage 33, and the flow passage 203 of the third port P3, the flow passage 204 of the fourth port P4 and the flow passage 205 of the fifth port P5 communicate with one another through the second flow passage 34, whereas the flow passage 206 of the sixth port P6 is being sealed with the outer peripheral surface of the barrel part 30. At this position, the first port P1 and the second port P2 are in the open state, and the third port P3, the fourth port P4 and the fifth port P5 are also in the open state, whereas the sixth port P6 is in the closed state.

The third position is present in the middle of the movement of the cock member 3 from the first position shown in FIG. 6 to the second position shown in FIG. 13.

Figure 12:
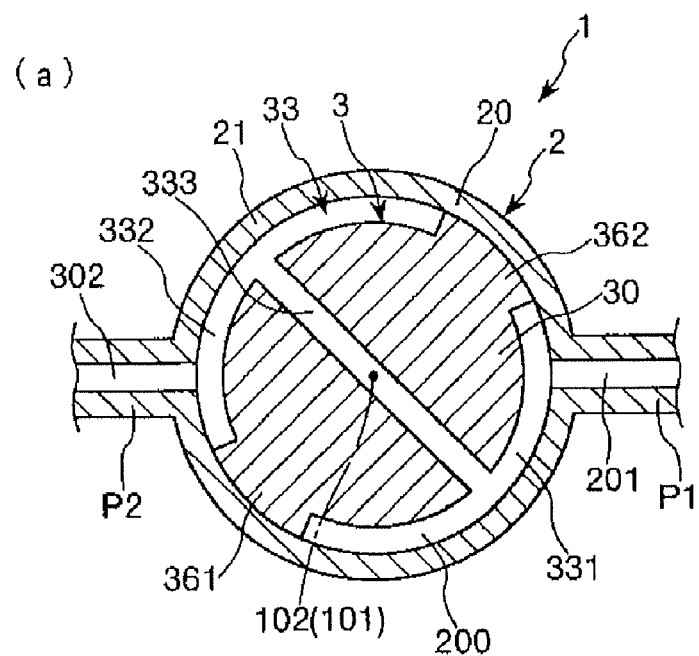
FIG. 12 illustrates cross-sectional views for schematically illustrating a flow passage changeover pattern in the multiway cock shown in FIG. 3.
Figure 12:
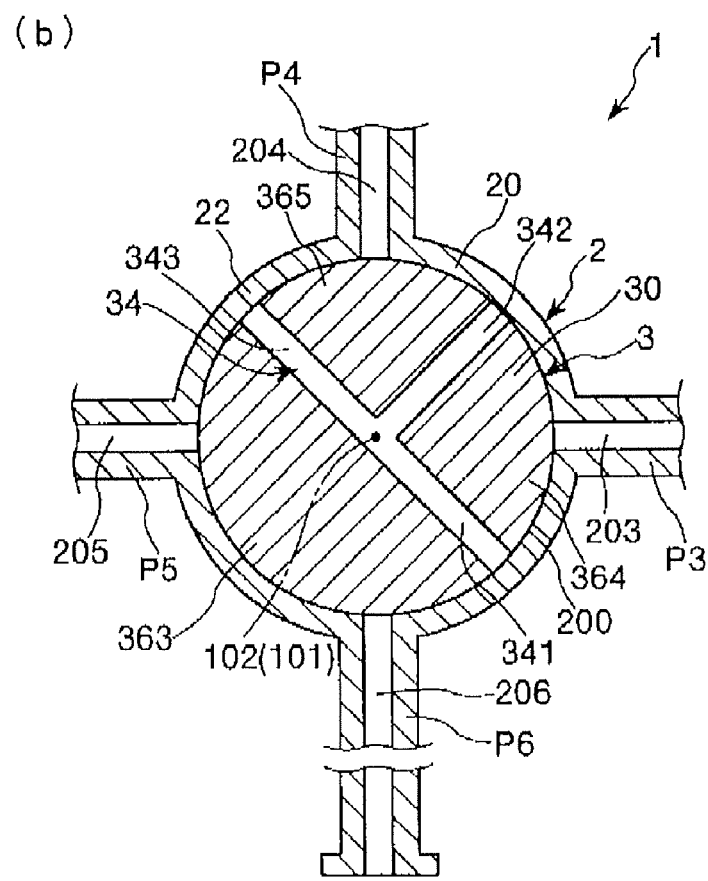

[6] When the cock member 3 is further rotated clockwise in FIG. 3 and positioned in a fifth position shown in FIG. 12, the flow passage 201 of the first port P1 and the flow passage 202 of the second port P2 communicate with each other through the first flow passage 33, whereas the flow passage 203 of the third port P3, the flow passage 204 of the fourth port P4, the flow passage 205 of the fifth port P5 and the flow passage 206 of the sixth port P6 are each being sealed with the outer peripheral surface of the barrel part 30. At this position, the first port P1 and the second port P2 are in the open state, whereas the third port P3, the fourth port P4, the fifth port P5 and the sixth port P6 are each in the closed state.

The fifth position is located in the course of the movement of the cock member 3 from the third position shown in FIG. 11 to the second position shown in FIG. 13 (in the example shown in the figures, the fifth position is located in the middle of the movement from the third position to the second position).

Incidentally, description of the operation during the movement of the cock member 3 from the fifth position to the second position is omitted.

[7] When the cock member 3 is further rotated clockwise in FIG. 3 so as to position the lever 32 of the cock member 3 in the same direction as the first port P1 and the third port P3 as shown in FIG. 3, the projection 311 of the cock member 3 abuts on the end portion on the right side in FIG. 3 of the projection 23 of the cock body 2, so that the cock member 3 cannot be rotated any more clockwise in FIG. 3. In this instance, as shown in FIG. 13, the cock member 3 is positioned in the second position, where the flow passage 201 of the first port P1, the flow passage 202 of the second port P2 and the flow passage 205 of the fifth port P5 are each being sealed with the outer peripheral surface of the barrel part 30, whereas the flow passage 203 of the third port P3, the flow passage 204 of the fourth port P4 and the flow passage 206 of the sixth port P6 communicate with one another through the second flow passage 34. At this position, the first port P1, the second port P2 and the fifth port P5 are each in the closed state, whereas the third port P3, the fourth port P4 and the sixth port P6 are in the open state.

In addition, when the cock member 3 is rotated counterclockwise in FIG. 3 from the second position, contrary to the above-mentioned, operations reverse to the above-mentioned operations are executed. Part of this will be described below.

[8] For example, when the cock member 3 is rotated counterclockwise in FIG. 3 to be positioned in the position shown in FIG. 9, the flow passage 201 of the first port P1 and the flow passage 202 of the second port P2 communicate with each other through the first flow passage 33, whereas the flow passage 203 of the third port P3, the flow passage 204 of the fourth port P4, the flow passage 205 of the fifth port P5 and the flow passage 206 of the sixth port P6 are each sealed with the outer peripheral surface of the barrel part 30. At this position, the first port P1 and the second port P2 are in the open state, whereas the third port P3, the fourth port P4, the fifth port P5 and the sixth port P6 are each in the closed state.

[9] When the cock member 3 is further rotated counterclockwise in FIG. 3 to be positioned in the position shown in FIG. 8, the flow passage 201 of the first port P1 and the flow passage 202 of the second port P2 are changed over to the state of being sealed with the outer peripheral surface of the barrel part 30, whereas the flow passage 203 of the third port P3, the flow passage 204 of the fourth port P4, the flow passage 205 of the fifth port P5 and the flow passage 206 of the sixth port P6 are each maintained in the state of being sealed with the outer peripheral surface of the barrel part 30. At this position, the first port P1 and the second port P2 are each changed over from the open state to the closed state, whereas the third port P3, the fourth port P4, the fifth port P5 and the sixth port P6 are each maintained in the closed state.

[10] When the cock member 3 is further rotated slightly counterclockwise in FIG. 3 to be positioned in the position shown in FIG. 7 is a condition immediately before the flow passage 204 of the fourth port P4, the flow passage 205 of the fifth port P5 and the flow passage 206 of the sixth port P6 come to communicate with one another through the second flow passage 34. Immediately after this condition, the flow passage 204 of the fourth port P4, the flow passage 205 of the fifth port P5 and the flow passage 206 of the sixth port P6 are changed over to the state of communicating with one another through the second flow passage 34, whereby the fourth port P4, the fifth port P5 and the sixth port P6 are each changed over from the closed state to the open state.

When the cock member 3 is thus rotated (subjected to a rotating operation) counterclockwise in FIG. 3, the timing of transition of the first port P1 and the second port P2 from the open state to the closed state is close to the timing of transition of the fourth port P4, the fifth port P5 and the sixth port P6 from the closed state to the open state, and the fourth port P4, the fifth port P5 and the sixth port P6 transit from the closed state to the open state occurs after the first port P1 and the second port P2 transit from the open state to the closed state.

Incidentally, the foregoing is relevant to the case where a>b. In the case where a=b, when the cock member 3 is rotated (subjected to a rotating operation) counterclockwise in FIG. 3, the timing of transition of the first port P1 and the second port P2 from the open state to the closed state and the timing of transition of the fourth port P4, the fifth port P5 and the sixth port P6 from the open state to the closed state are the same.

Now, the liquid dispensing circuit 10 will be described below.

As shown in FIGS. 1 and 2, the liquid dispensing circuit 10 includes the above-described multiway cock 1, the tubes 61 to 68, the check valves 71 to 73, the three-way cock (medicine dispensing cock) 74, the air vent integrated type bottle needles 75, 76, and a branch connector 77 composed of a three-way branch pipe (T-pipe, Y-pipe, non-right angled T-pipe, or the like), and a casing 81 for accommodating a part (most part) of these components. The inner cavities of the tubes 61 to 68 and the like constitute flow passages.

Further, in the configuration shown in the figures, as the check valves 71 and 73, those which permit tubes to be connected (linked) to both end portions thereof are used. In addition, as the check valve 72, one which is provided with a female luer taper at one end portion thereof and with a male luer taper at the other end portion thereof is used. Further, a port, on the side of connection with the check valve 72, of the branch connector 77 is formed with a female luer taper, and the remaining two ports are tapered so that tubes can be connected thereto. Further, the casing 81 has a flat box-like shape with rounded corner portions.

The multiway cock 1 is stationarily disposed in the casing 81 so that the lever 32 thereof is located on the outside of a wall part 811 on the upper side in FIG. 1 of the casing 81.

The first port P1 of the multiway cock 1 is connected to a flow passage communicating with a blood vessel of a patient (a person for whom the circuit is used).

Specifically, the first port P1 is connected (linked) with the base end side (one end side) of the tube 61, and the tip end side (other end side) of the tube 61 is connected to one port of the branch connector 77.

In addition, the second port P2 is connected to a flow passage communicating with a pressure sensor (pressure detecting means) which is not shown.

Specifically, the second port P2 is connected with the base end side of the tube 62. The tube 62 is, from its intermediate portion to its tip end, disposed on (led out to) the outside of the casing 81, and the tip end side of the tube 62 is connected to the pressure sensor. The pressure sensor measures (detects), for example, an arterial blood pressure (blood pressure in a coronary artery) or the like, and the measurement result (detection result) is displayed on a monitor (display means) which is not shown.

In addition, the third port P3 is connected to a flow passage communicating with a vessel (vial or the like) in which a radiopaque material is contained (not shown).

Specifically, the third port P3 is connected with the base end side of the tube 63, the tip end side of the tube 63 is connected to one end side of the check valve 71, and the other end side of the check valve 71 is connected with the base end side of the tube 64. The tube 64 is, from its intermediate portion to its tip end, disposed on the outside of the casing 81, and the tip end side of the tube 64 is connected with the air vent integrated type bottle needle 75. The bottle needle 75 is connected to the vessel (not shown) in which the radiopaque material is contained.

In addition, the check valve 71 is provided so as to permit a liquid (fluid) to flow in the direction from the side of the bottle needle 75 (radiopaque material) toward the side of the third port P3 (multiway cock 1) and inhibit the liquid from flowing in the reverse direction. Incidentally, the arrows with parentheses in the vicinity of the check valves 71 to 73 in FIG. 2 show the directions in which a liquid is permitted to flow.

Further, the fourth port P4 is connected to a flow passage leading to a patient's blood vessel.

Specifically, the fourth port P4 is connected with the female luer taper on the one end side of the check valve 72, the male luer taper on the other end side of the check valve 72 is connected to the female luer taper formed at one of the other two ports of the branch connector 77, and the other port of the branch connector 77 is connected with the base end side of the tube 65. The tube 65 is, from its intermediate portion to its tip end, disposed on the outside of the casing 81, and the tip end side of the tube 65 is connected to one port of the three-way cock (medicine dispensing cock) 74. Another port of the three-way cock 74 is connected with the base end side of the tube 66, and the tip end side of the tube 66 is connected to the proximal side of a catheter (tube) which is not shown. The distal side of the catheter is inserted in the patient's blood vessel, to reach the vicinity of a stenosed part (target part) of a coronary artery through the blood vessel.

In addition, the check valve 72 is provided so as to permit a liquid (fluid) to flow in the direction from the side of the fourth port P4 (the multiway cock 1) toward the side of the branch connector 77 (the patient), and inhibit the liquid from flowing in the reverse direction.

Further, of the three ports of the three-way cock 74, the one not connected to anything (the remaining port) is used, for example, in the case of dispensing a medicine such as nitroglycerine, in the case of drawing blood (arterial blood), or in other cases.

In addition, the fifth port P5 is connected to a flow passage communicating with a vessel (bag, bottle or the like) in which physiological saline is contained (not shown).

Specifically, the fifth port P5 is connected with the base end side of the tube 67, the tip end side of the tube 67 is connected to one end side of the check valve 73, and the other end side of the check valve 73 is connected with the base end side of the tube 68. The tube 68 is, from its intermediate portion to its tip end, disposed on the outside of the casing 81, and the tip end side of the tube 68 is connected with the air vent integrated type bottle needle 76. The bottle needle 76 is connected to the vessel (not shown) in which the physiological saline is contained.

Further, the check valve 73 is provided so as to permit a liquid to flow in the direction from the side of the bottle needle 76 (physiological saline) toward the fifth port P5 (the multiway cock 1), and inhibit the liquid from flowing in the reverse direction.

Here, it is preferable that the bottle needle 75 and the bottle needle 76 or the tube 64 and the tube 68 are color-coded. This makes it possible to prevent misconnection of the bottle needles 75, 76. More specifically, the bottle needle 75 can infallibly be connected to the vessel in which the radiopaque material is contained, and the bottle needle 76 can infallibly be connected to the vessel in which the physiological saline is contained.

In addition, the sixth port P6 is connected to a syringe (liquid feeding means) 11 directly or through a tube (flow passage) or the like.

Specifically, the sixth port P6 is connected directly with the syringe 11. In this case, the casing 81 is formed with an opening in its portion corresponding to the sixth port P6, specifically, in the periphery (vicinity) of a tip portion of the sixth port P6 so that the syringe 11 can be inserted through the opening into the inside of the casing 81 and connected to the sixth port P6.

Further, the casing 81 is provided with a plate-like guide part 82 in the vicinity of the sixth port P6. The guide part 82 is so formed as to project from an end portion of a wall part (a wall part on the opposite side from the wall part on the side where the lever 32 is disposed) 812 on the lower side in FIG. 1 of the casing 81 toward the tip end of the sixth port P6, and to be parallel to the axis of the sixth port P6 and the wall parts 811 and 812. The guide part 82 ensures that, when the syringe 11 is connected to the sixth port P6, the syringe 11 can be prevented from shaking, and the syringe 11 can be operated assuredly.

Now, operations (method of use) of the liquid dispensing circuit 10 will be described below referring to FIGS. 2, 6, 10, 12 and 13.

In the case of dispensing physiological saline into a patient, first, the position of the lever 32 of the cock member 3 is set to the same direction as the second port P2 and the fifth port P5, whereby the cock member 3 is positioned into the first position. With this arrangement, as shown in FIG. 6, the first port P1, the second port P2 and the third port P3 are each in the closed state, whereas the fourth port P4, the fifth port P5 and the sixth port P6 are in the open state. In this condition, the connection between a patient's artery and the pressure sensor (not shown) is cut off.

Next, a plunger 111 of the syringe 11 is moved toward the base end. As a result, the physiological saline in the vessel (not shown) is introduced into the syringe 11 through the bottle needle 76, the tube 68, the check valve 73, the tube 67 and the multiway cock 1. In this case, the check valve 72 functions to inhibit the patient's blood from flowing toward the side of the syringe 11.

Subsequently, the plunger 111 of the syringe 11 is moved toward the tip end. Thus, the physiological saline in the syringe 11 flows out through the multiway cock 1, the check valve 72, the branch connector 77, the tube 65, the three-way cock 74, the tube 66 and the catheter (not shown) into the vicinity of a stenosed part of the patient's coronary artery.

Thus, after the cock member 3 is positioned into the first position, the physiological saline can be continuously sucked in and discharged by only operating the syringe 11, without operating the lever 32.

Further, in the case of dispensing a radiopaque material into a patient, first, the position of the lever 32 of the cock member 3 is set to the same direction as the first port P1 and the third port P3, whereby the cock member 3 is positioned into the second position. At this position, as shown in FIG. 13, the first port P1, the second port P2 and the fifth port P5 are each in the closed state, whereas the third port P3, the fourth port P4 and the sixth port P6 are in the open state. Consequently, in this condition, the connection between the patient's artery and the pressure sensor is cut off.

Next, the plunger 111 of the syringe 11 is moved toward the base end. Then, the radiopaque material in the vessel (not shown) is introduced into the syringe 11 through the bottle needle 75, the tube 64, the check valve 71, the tube 63 and the multiway cock 1. In this case, the check valve 72 functions to inhibit the patient's blood from flowing toward the side of the syringe 11.

Subsequently, the plunger 111 of the syringe 11 is moved toward the tip end. Thus, the radiopaque material in the syringe 11 flows out through the multiway cock 1, the check valve 72, the branch connector 77, the tube 65, the three-way cock 74, the tube 66 and the catheter into the vicinity of the stenosed part of the patient's coronary artery.

Thus, after the cock member 3 is positioned into the second position, the radiopaque material can be continuously sucked in and discharged by only operating the syringe 11, without operating the lever 32.

Further, in the case of measuring the patient's arterial blood pressure (blood pressure in the coronary artery) and displaying the measurement result on the monitor (not shown), when the cock member 3 is positioned in the first position, the cock member 3 is shifted into the fourth position shown in FIG. 10. At this position, the first port P1 and the second port P2 are put in the open state, whereas the third port P3, the fourth port P4, the fifth port P5 and the sixth port P6 are each put in the closed state. Consequently, the patient's artery and the pressure sensor are connected with each other. The patient's arterial blood pressure is measured by the pressure sensor through the catheter, the tube 66, the three-way cock 74, the tube 65, the branch connector 77, the tube 61, the multiway cock 1 and the tube 62, and the measurement result is displayed on the monitor.

In addition, when the cock member 3 is positioned in the second position, the cock member 3 is moved into the fifth position shown in FIG. 12. At this position, that the first port P1 and the second port P2 are put in the open state, whereas the third port P3, the fourth port P4, the fifth port P5 and the sixth port P6 are each put in the closed state, and the patient's arterial blood pressure is displayed on the monitor, in the same manner as above.

As has been described above, according to the multiway cock 1 and the liquid dispensing circuit 10, it is possible by only rotating the single lever 32 (cock member 3) to freely select the opening/closing of the first to sixth ports P1 to P6 and thereby to change over the complicate flow passages easily and speedily.

Specifically, when the cock member 3 is positioned in the first position, the physiological saline can be continuously sucked in and discharged by only operating the syringe 11, without operating the lever 32. In addition, when the cock member 3 is positioned in the second position, the radiopaque material can be continuously sucked in and discharged by only operating the syringe 11, without operating the lever 32. Further, when the cock member 3 is positioned in the fourth position or the fifth position, the patient's arterial blood pressure can be measured and displayed on the monitor.

Further, in the multiway cock 1, the first portion 21 and the second portion 22 are juxtaposed to each other along the axis 101 of the hollow cylindrical part 20, achieving reduction in size.

While the multiway cock and the liquid dispensing circuit according to the present invention have been described above, based on the embodiment shown in the drawings, the invention is not limited to the embodiment. The configuration of each component can be replaced by an arbitrary configuration having a function equivalent to the function of the original configuration. Further, other arbitrary structures may be added to the present invention.

Incidentally, in the present invention, the number of the ports provided in the outer periphery of the first portion of the tubular part of the cock body may not necessarily be two, and may be three or more.

In addition, in the present invention, the number of the ports provided in the outer periphery of the second portion of the tubular part of the cock body may not necessarily be four, and may be three or be five or more.

Further, in the present invention, the number of the portions of the tubular part of the cock body which are provided with the ports may not necessarily be two (the first portion and the second portion), and may be three or more. Similarly, the number of the flow passages formed in the barrel part of the cock member may not necessarily be two (the first flow passage and the second flow passage), and may be three or more.

Specifically, in the present invention, a configuration may be adopted in which, for example, the tubular part of the cock body further has a third portion provided with at least two ports in the outer periphery thereof, the barrel part of the cock member is provided further with a third flow passage for opening in a predetermined combination the ports provided in the third portion, and opening/closing of the ports provided in the first portion, the second portion and the third portion is selected by rotating the cock member. In this case, preferably, the third portion is provided in the manner of being aligned with the first portion and the second portion along the axis (center axis) of the tubular portion. Further, it is preferable that the third flow passage communicates with neither of the first flow passage and the second flow passage.

In addition, the use for the multiway cock and the liquid dispensing circuit according to the present invention is not particularly limited. The multiway cock and the liquid dispensing circuit can be applied not only to the above-described embodiment but also to, for example, the cases where a multiplicity of tubes are used, such as anesthetic procedures.

Industrial Applicability

According to the present invention, the tubular part of the cock body has the first portion and the second portion each provided with a group of ports, and the common (single) cock member is provided for selecting the opening/closing of the ports. Therefore, complicate flow passages can be changed over easily and speedily. Further, since the first portion and the second portion are juxtaposed to each other along the axis of the tubular part, a reduction in size can be achieved. Accordingly, the present invention has industrial applicability.

The invention claimed is:

1. A multiway cock comprising:
a cock body including a tubular part which has a first portion and a second portion juxtaposed to each other along an axis, at least two ports provided in an outer periphery of the first portion, and at least three ports provided in an outer periphery of the second portion; and
a cock member having a barrel part rotatably inserted in the tubular part, the barrel part being formed with a first flow passage for opening in a predetermined combination the ports provided in the first portion, and a second flow passage for opening in a predetermined combination the ports provided in the second portion, wherein
opening or closing of the ports provided in the first portion and the second portion is selected by rotating the cock member
the first flow passage is so formed that predetermined two of the ports provided in the first portion can simultaneously be put into an open state or a closed state,
the second flow passage is so formed that predetermined three of the ports provided in the second portion can simultaneously be put into an open state or a closed state, and
in an operation of rotating the cock member, the timing of transition of the predetermined two ports in the first portion from the closed state to the open state is close to the timing of transition of the predetermined three ports in the second portion from the open state to the closed state, and the predetermined two ports in the first portion transit from the closed state to the open state occurs after the predetermined three ports in the second portion transit from the open state to the closed state.

2. The multiway cock according to claim 1, wherein the first flow passage is so formed that a rotating angle range of the cock member where the predetermined two ports are in the open state is wider than a rotating angle range of the cock member where the predetermined two ports are in the closed state.

3. The multiway cock according to claim 1, wherein
the second flow passage is so formed that a rotating angle range of the cock member where the predetermined three ports are in the closed state is wider than a rotating angle range of the cock member where the predetermined three ports are in the open state.

4. The multiway cock according to claim 1, wherein
the predetermined two ports in the first portion are in the closed state when the predetermined three ports in the second portion are in the open state.

5. The multiway cock according to claim 1, wherein
the first flow passage has a first part provided in an outer peripheral surface of the barrel part and extended in the circumferential direction of the barrel part, a second part located on an opposite side of a center axis of the barrel part from the first part and extended in the circumferential direction of the barrel part, and a third part which penetrates the barrel part and connects the first part to the second part.

6. A multiway cock comprising:
a cock body including a tubular part which has a first portion, and a second portion juxtaposed to each other along an axis, at least two ports provided in an outer periphery of the first portion, and at least three ports provided in an outer periphery of the second portion; and
a cock member having a barrel part rotatably inserted in the tubular part, the barrel part being formed with a first flow passage for opening in a predetermined combination the ports provided in the first portion, and a second flow passage for opening in a predetermined combination the ports provided in the second portion, wherein
opening or closing of the ports provided in the first ortion and the second portion is selected by rotating the cock member, wherein
the cock body has, in the outer periphery of the first portion, a first port and a second port arranged side by side along the circumferential direction thereof, and in the outer periphery of the second portion, a third port, a fourth port, a fifth port and a sixth port arranged sequentially side by side along a circumferential direction thereof,
the first port, the second port and the third port are each in a closed state whereas the fourth port, the fifth port and the sixth port are each in an open state when the cock member is positioned in a first position, and
the first port, the second port and the fifth port are each in the closed state whereas the third port, the fourth port and the sixth port are each in the open state when the cock body is positioned in the second position.

7. The multiway cock according to claim 6, wherein the first flow passage is so formed that predetermined two of the ports provided in the first portion can simultaneously be put into an open state or a closed state, and that a rotating angle range of the cock member where the predetermined two ports are in the open state is wider than a rotating angle range of the cock member where the predetermined two ports are in the closed state.

8. The multiway cock according to claim 6, wherein
the second flow passage is so formed that predetermined three of the ports provided in the second portion can simultaneously be put into an open state or a closed state, and that a rotating angle range of the cock member where the predetermined three ports are in the closed state is wider than a rotating angle range of the cock member where the predetermined three ports are in the open state.

9. The multiway cock according to claim 6, wherein
the first flow passage is so formed that predetermined two of the ports provided in the first portion can simultaneously be put into a closed state,
the second flow passage is so formed that predetermined three of the ports provided in the second portion can simultaneously be put into an open state, and
the predetermined two ports in the first portion are in the closed state when the predetermined three ports in the second portion are in the open state.

10. The multiway cock according to claim 6, wherein
the first flow passage is so formed that predetermined two of the ports provided in the first portion can simultaneously be put into an open state or a closed state,
the second flow passage is so formed that predetermined three of the ports provided in the second portion can simultaneously be put into an open state or a closed state, and
in an operation of rotating the cook member, the timing of transition of the predetermined two ports in the first portion from the closed state to the open state and the timing of transition of the predetermined three ports in the second portion from the open state to the closed state are the same.

11. The multiway cock according to claim 6, wherein
the first flow passage has a first part provided in an outer peripheral surface of the barrel part and extended in the circumferential direction of the barrel part, a second part located on an opposite side of a center axis of the barrel part from the first part and extended in the circumferential direction of the barrel part, and a third part which penetrates the barrel part and connects the first part to the second part.

12. A liquid dispensing circuit comprising a multiway cock comprising:
a cock body including a tubular part which has a first portion and a second portion juxtaposed to each other along an axis, at least two ports provided in the outer periphery of the first portion, and at least three ports provided in an outer periphery of the second portion; and
a cock member having a barrel part rotatably inserted in the tubular part, the barrel part being formed with a first flow passage for opening in a predetermined combination the ports provided in the first portion, and a second flow passage for opening in a predetermined combination the ports provided in the second portion, wherein
opening or closing of the ports provided in the first portion and the second portion is selected by rotating the cock member,
the first flow passage is so formed that predetermined two of the ports provided in the first portion can simultaneously be put into an open state or a closed state,
the second flow passage is so formed that predetermined three of the ports provided in the second portion can simultaneously be put into an open state or a closed state, and
in an operation of rotating the cock member, the timing of transition of the predetermined two ports in the first portion from the closed state to the open state is close to the timing of transition of the predetermined three ports in the second portion from the open state to the closed state, and the predetermined two ports in the first portion transit from the closed state to the open state occurs after the predetermined three ports in the second portion transit from the open state to the closed state.

13. A liquid dispensing circuit comprising a multiway cock comprising:
a cock body including a tubular part which has a first portion and a second portion juxtaposed each other along an axis, at least two ports provided in the outer periphery of the first portion, and at least three ports provided in an outer periphery of the second portion; and
a cock member having a barrel part rotatably inserted in the tubular part, the barrel part being formed with a first flow passage for opening in a predetermined combination the ports provided in the first portion, and a second flow passage for opening in a predetermined combination the ports provided in the second portion, wherein
opening or closing of the ports provided in the first portion and the second portion is selected by rotating the cock member,
the cock body has, in the outer periphery of the first portion, a first port and a second port arranged side by side along the circumferential direction thereof, and in the outer periphery of the second portion, a third port, a fourth port, a fifth port and a sixth port arranged sequentially side by side along a circumferential direction thereof,
the first port, the second port and the third port are each in a closed state whereas the fourth port, the fifth port and the sixth port are each in an open state when the cock member is positioned in a first position, and
the first port, the second port and the fifth port are each in the closed state whereas the third port, the fourth port and the sixth port are each in the open state when the cock body is positioned in the second position.

* * * * *